United States Patent
DeLuca et al.

(10) Patent No.: US 6,392,071 B1
(45) Date of Patent: *May 21, 2002

(54) 26,27-HOMOLOGATED-20-EPI-2-ALKYLIDENE-19-NOR-VITAMIN D COMPOUNDS

(75) Inventors: Hector F. DeLuca, Deerfield, WI (US); Rafal R. Sicinski, Warsaw (PL)

(73) Assignee: Wisconsin Alumni Research Foundation, Madison, WI (US)

(*) Notice: Subject to any disclaimer, the term of this patent is extended or adjusted under 35 U.S.C. 154(b) by 0 days.

This patent is subject to a terminal disclaimer.

(21) Appl. No.: 09/540,686

(22) Filed: Mar. 31, 2000

Related U.S. Application Data

(60) Continuation-in-part of application No. 09/370,966, filed on Aug. 10, 1999, now abandoned, which is a continuation of application No. 09/151,113, filed on Sep. 10, 1998, now Pat. No. 5,936,133, which is a division of application No. 08/819,693, filed on Mar. 17, 1997, now Pat. No. 5,843,928.

(51) Int. Cl.[7] ................ C07C 401/00; A61K 31/593
(52) U.S. Cl. .................. 552/653; 552/653; 514/167
(58) Field of Search ................. 514/167; 553/653

(56) References Cited

U.S. PATENT DOCUMENTS 4,800,198 A * 1/1989 DeLuca et al. ............. 514/167

(List continued on next page.)

FOREIGN PATENT DOCUMENTS

WO   WO 98/41501   9/1998

OTHER PUBLICATIONS

Sicinski et al, "New 1α,25–Dihydroxy–19–Norvitamin $D_3$ Compounds of High Biological Activity: Synthesis and Biological Evaluation of 2–Hydroxymethyl, 2–Methyl, and 2–Methylene Analogues", J. Med. Chem.,pp. 4662–4674, 1998.

(List continued on next page.)

Primary Examiner—Sabiha Qazi
(74) Attorney, Agent, or Firm—Andrus, Sceales, Starke & Sawall, LLP

(57) ABSTRACT

This invention provides a novel class of vitamin D related compounds, namely, the 2-alkylidene-19-nor-vitamin D derivatives, as well as a general method for their chemical synthesis. The compounds have the formula:

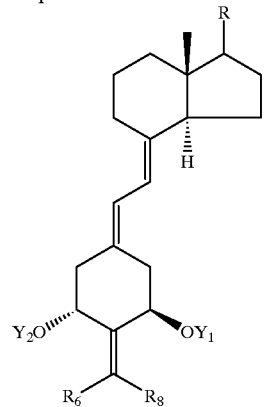

where $Y_1$ and $Y_2$, which may be the same or different, are each selected from the group consisting of hydrogen and a hydroxy-protecting group, $R_6$ and $R_8$, which may be the same or different, are each selected from hydrogen, alkyl, hydroxyalkyl and fluoroalkyl, or when taken together represent the group —$(CH_2)_x$— where x is an integer from 2 to 5, and where the group R represents any of the typical side chains known for vitamin D type compounds. These 2-substituted compounds are characterized by relatively high intestinal calcium transport activity and relatively high bone calcium mobilization activity resulting in novel therapeutic agents for the treatment of diseases where bone formation is desired, particularly low bone turnover osteoporosis. These compounds also exhibit pronounced activity in arresting the proliferation of undifferentiated cells and inducing their differentiation to the monocyte thus evidencing use as anti-cancer agents and for the treatment of diseases such as psoriasis.

9 Claims, 2 Drawing Sheets

U.S. PATENT DOCUMENTS

| | | | |
|---|---|---|---|
| 4,851,401 A | | 7/1989 | DeLuca et al. ............. 514/167 |
| 5,089,641 A | * | 2/1992 | DeLuca et al. ............. 552/653 |
| 5,587,497 A | * | 12/1996 | DeLuca et al. ............. 552/653 |
| 5,936,105 A | | 8/1999 | Paaren ....................... 552/653 |
| 5,945,410 A | | 8/1999 | DeLuca et al. ............. 514/167 |
| 5,981,780 A | | 11/1999 | DeLuca ...................... 552/653 |

OTHER PUBLICATIONS

Yang et al, "20–Epi Analogues of 1,25–Dihydroxyvitamin $D_3$ are Highly Potent Inducers of DRIP Coactivator Complex Binding to the Vitamin $D_3$ Receptor", Journal of Biological Chemistry, pp. 16838–16845, 1999.

* cited by examiner

26,27-HOMOLOGATED-20-EPI-2-ALKYLIDENE-19-NOR-VITAMIN D COMPOUNDS

CROSS-REFERENCE TO RELATED APPLICATIONS

This application s a continuation-in-part of application Ser. No. 09/370,966 filed Aug. 10, 1999 now abandoned, which in turn is a continuation of Ser. No. 09/151,113, filed Sep. 10, 1998, now U.S. Pat. No. 5,936,133, which in turn is a division of application Ser. No. 08/819,693, filed Mar. 17, 1997, now U.S. Pat. No. 5,843,928.

STATEMENT REGARDING FEDERALLY SPONSORED RESEARCH OR DEVELOPMENT

This invention was made with United States government support awarded by the following agencies:
NIH DK 14881-26S1
The United States has certain rights in this invention.

BACKGROUND OF THE INVENTION

This patent invention relates to vitamin D compounds, and more particularly to vitamin D derivatives substituted at the carbon 2 position.

The natural hormone, $1\alpha,25$-dihydroxy vitamin $D_3$ and its analog in ergosterol series, i.e. $1\alpha,25$-dihydroxyvitamin $D_2$ are known to be highly potent regulators of calcium homeostasis in animals and humans, and more recently their activity in cellular differentiation has been established, Ostrem et al., Proc. Natl. Acad. Sci. USA, 84, 2610 (1987). Many structural analogs of these metabolites have been prepared and tested, including $1\alpha$-hydroxyvitamin $D_3$, $1\alpha$-hydroxyvitamin $D_2$, various side chain homologated vitamins and fluorinated analogs. Some of these compounds exhibit an interesting separation of activities in cell differentiation and calcium regulation. This difference in activity may be useful in the treatment of a variety of diseases such as renal osteodystrophy, vitamin D-resistant rickets, osteoporosis, psoriasis, and certain malignancies.

Recently, a new class of vitamin D analogs has been discovered, i.e. the so called 19-nor-vitamin D compounds, which are characterized by the replacement of the A-ring exocyclic methylene group (carbon 19), typical of the vitamin D system, by two hydrogen atoms. Biological testing of such 19-nor-analogs (e.g., $1\alpha,25$-dihydroxy-19-nor-vitamin $D_3$) revealed a selective activity profile with high potency in inducing cellular differentiation, and very low calcium mobilizing activity. Thus, these compounds are potentially useful as therapeutic agents for the treatment of malignancies, or the treatment of various skin disorders. Two different methods of synthesis of such 19-nor-vitamin D analogs have been described (Perlman et al., Tetrahedron Lett. 31, 1823 (1990); Perlman et al., Tetrahedron Lett. 32, 7663 (1991), and DeLuca et al., U.S. Pat. No. 5,086,191).

In U.S. Pat. No. 4,666,634, $2\beta$-hydroxy and alkoxy (e.g., ED-71) analogs of $1\alpha,25$-dihydroxyvitamin $D_3$ have been described and examined by Chugai group as potential drugs for osteoporosis and as antitumor agents. See also Okano et al., Biochem. Biophys. Res. Commun. 163, 1444 (1989). Other 2-substituted (with hydroxyalkyl, e.g., ED-120, and fluoroalkyl groups) A-ring analogs of $1\alpha,25$-dihydroxyvitamin $D_3$ have also been prepared and tested (Miyamoto et al., Chem. Pharm. Bull. 41 1111 (1993); Nishii et al., Osteoporosis Int. Suppl. 1, 190 (1993); Posner et al., J. Org. Chem. 59, 7855 (1994), and J. Org. Chem. 60, 4617 (1995)).

Recently, 2-substituted analogs of $1\alpha,25$-dihydroxy-19-norvitamin $D_3$ have also been synthesized, i.e. compounds substituted at 2-position with hydroxy or alkoxy groups (DeLuca et al., U.S. Pat. No. 5,536,713), which exhibit interesting and selective activity profiles. All these studies indicate that binding sites in vitamin D receptors can accommodate different substituents at C-2 in the synthesized vitamin D analogs.

In a continuing effort to explore the 19-nor class of pharmacologically important vitamin D compounds, their analogs which are characterized by the presence of an alkylidene (particularly methylene) substituent at the carbon 2 (C-2), i.e. 2-alkylidene-19-nor-vitamin D compounds, have now been synthesized and tested. Of particular interest are the analogs which are characterized by the transposition of the ring A exocyclic methylene group, present in the normal vitamin D skeleton, from carbon 10 (C-10) to carbon 2 (C-2), i.e. 2-methylene-19-nor-vitamin D compounds. Such vitamin D analogs seemed interesting targets because the relatively small alkylidene (particularly methylene) group at C-2 should not interfere with vitamin D receptor. Moreover, molecular mechanics studies performed on the model $1\alpha$-hydroxy-2-methylene-19-nor-vitamins indicate that such molecular modification does not change substantially the conformation of the cyclohexanediol ring A. However, introduction of the 2-methylene group into 19-nor-vitamin D carbon skeleton changes the character of its $1\alpha$- and $3\beta$-A-ring hydroxyls. They are both now in the allylic positions, similarly, as $1\alpha$-hydroxyl group (crucial for biological activity) in the molecule of the natural hormone, $1\alpha,25$-$(OH)_2D_3$.

SUMMARY OF THE INVENTION

A class of $1\alpha$-hydroxylated vitamin D compounds not known heretofore are the 19-nor-vitamin D analogs having an alkylidene (particularly methylene) group at the 2-position, i.e. 2-alkylidene-19-nor-vitamin D compounds, particularly 2-methylene-19-nor-vitamin D compounds. These latter compounds are those in which the A-ring exocyclic methylene group typical of all vitamin D system has been transposed to the carbon 2, i.e. 19-nor-vitamin D analogs having a methylene group at the 2-position.
Structurally these novel analogs are characterized by the general formula I shown below:

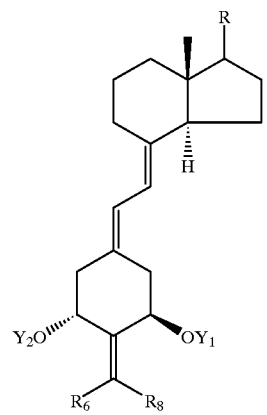

I where $Y_1$ and $Y_2$ which may be the same or different, are each selected from the group consisting of hydrogen and a hydroxy-protecting group, $R_6$ and $R_8$, which may be the same or different, are each selected from the group consisting of hydrogen, alkyl, hydroxyalkyl and fluoroalkyl, or, when taken together represent the group —(CH$_2$)$_x$— where X is an integer from 2 to 5, and where the group R represents any of the typical side chains known for vitamin D type compounds.

More specifically R can represent a saturated or unsaturated hydrocarbon radical of 1 to 35 carbons, that may be straight-chain, branched or cyclic and that may contain one or more additional substituents, such as hydroxy- or protected-hydroxy groups, fluoro, carbonyl, ester, epoxy, amino or other heteroatomic groups. Preferred side chains of this type are represented by the structure below

where the stereochemical center (corresponding to C-20 in steroid numbering) may have the R or S configuration, (i.e. either the natural configuration about carbon 20 or the 20-epi configuration), and where Z is selected from Y, —OY, —CH$_2$OY, —C≡CY, CH=CHY, and —CH$_2$CH$_2$CH=CR$^3$R$^4$, where the double bond may have the cis or trans geometry, and where Y is selected from hydrogen, methyl, —COR$^5$ and a radical of the structure:

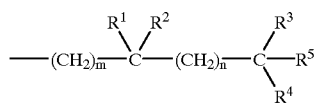

where m and n, independently, represent the integers from 0 to 5, where R$^1$ is selected from hydrogen, deuterium, hydroxy, protected hydroxy, fluoro, trifluoromethyl, and C$_{1-5}$-alkyl, which may be straight chain or branched and, optionally, bear a hydroxy or protected-hydroxy substituent, and where each of R$^2$, R$^3$, and R$^4$, independently, is selected from deuterium, deuteroalkyl, hydrogen, fluoro, trifluoromethyl and C$_{1-5}$ alkyl, which may be straight-chain or branched, and optionally, bear a hydroxy or protected-hydroxy substituent, and where R$^1$ and R$^2$, taken together, represent an oxo group, or an alkylidene group, =CR$^2$R$^3$, or the group —(CH$_2$)$_p$—, where p is an integer from 2 to 5, and where R$^3$ and R$^4$, taken together, represent an oxo group, or the group —(CH$_2$)$_q$—, where q is an integer from 2 to 5, and where R$^5$ represents hydrogen, hydroxy, protected hydroxy, C$_{1-5}$ alkyl or —OR$^7$ where R$^7$ represents C$_{1-5}$ alkyl, and wherein any of the CH-groups at positions 20, 22, or 23 in the side chain may be replaced by a nitrogen atom, or where any of the groups —CH(CH$_3$)—, —CH(R$^3$)—, or —CH(R$^2$)— at positions 20, 22, and 23, respectively, may be replaced by an oxygen or sulfur atom.

The wavy line to the methyl substituent at C-20 indicates that carbon 20 may have either the R or S configuration.

Specific important examples of side chains with natural 20R-configuration are the structures represented by formulas (a), b), (c), (d) and (e) below. i.e. the side chain as it occurs in 25-hydroxyvitamin D$_3$ (a); vitamin D$_3$ (b); 25-hydroxyvitamin D$_2$ (c); vitamin D$_2$ (d); and the C-24 epimer of 25-hydroxyvitamin D$_2$ (e):

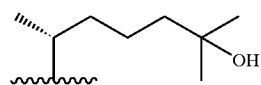
(a)

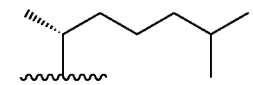
(b)

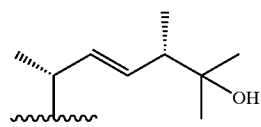
(c)

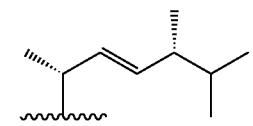
(d)

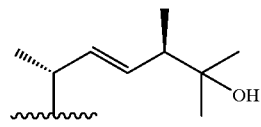
(e)

Specific important examples of side chains with the unnatural 20(S) (also referred to as the 20-epi) configuration are the structures represented by formulas (f), (g), (h), and (i) below:

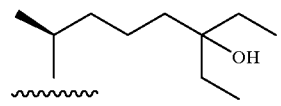
(f)

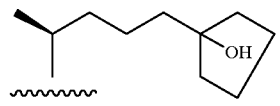
(g)

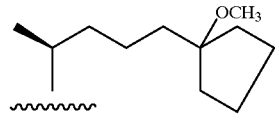
(h)

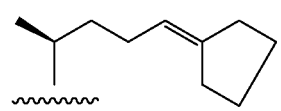
(i)

The above novel compounds exhibit a desired, and highly advantageous, pattern of biological activity. These compounds are characterized by relatively high intestinal calcium transport activity, as compared to that of 1α,25-dihydroxyvitamnin D$_3$, while also exhibiting relatively high activity, as compared to 1α,25-dihydroxyvitamin D$_3$, in their ability to mobilize calcium from bone. Hence, these compounds are highly specific in their calcemic activity. Their preferential activity on mobilizing calcium from bone and either high or normal intestinal calcium transport activity allows the in vivo administration of these compounds for the treatment of metabolic bone diseases where bone loss is a major concern. Because of their preferential calcemic activity on bone, these compounds would be preferred therapeutic agents for the treatment of diseases where bone formation is desired, such as osteoporosis, especially low bone turnover osteoporsis, steroid induced osteoporosis, senile osteoporosis or postmenopausal osteoporosis, as well as osteomalacia and renal osteodystrophy. The treatment may be transdermal, oral or parenteral. The compounds may be present in a composition in an amount from about 0.1 µg/gm to about 50 µg/gm of the composition, and may be administered in dosages of from about 0.1 µg/day to about 50 µg/day.

The compounds of the invention are also especially suited for treatment and prophylaxis of human disorders which are characterized by an imbalance in the immune system, e.g. in autoimmune diseases, including multiple sclerosis, diabetes mellitus, host versus graft reaction, and rejection of transplants; and additionally for the treatment of inflammatory diseases, such as rheumatoid arthritis and asthma, as well as the improvement of bone fracture healing and improved bone grafts. Acne, alopecia, skin conditions such as dry skin (lack of dermal hydration), undue skin slackness (insufficient skin firmness), insufficient sebum secretion and wrinkles, and hypertension are other conditions which may be treated with the compounds of the invention.

The above compounds are also characterized by high cell differentiation activity. Thus, these compounds also provide therapeutic agents for the treatment of psoriasis, or as an anti-cancer agent, especially against leukemia, colon cancer, breast cancer and prostate cancer. The compounds may be present in a composition to treat psoriasis in an amount from about 0.01 µg/gm to about 100 µg/gm of the composition, and may be administered topically, transdermally, orally or parenterally in dosages of from about 0.01 µg/day to about 100 µg/day.

This invention also provides novel intermediate compounds formed during the synthesis of the end products. Structurally, these novel intermediates are characterized by the general formulae V, VI, VII, VIII, IX and X below where $Y_1$, $Y_2$, $R_6$ and $R_8$ are as previously defined herein.

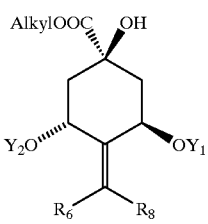

V

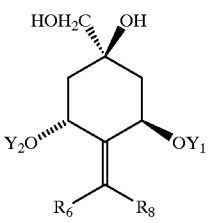

VI

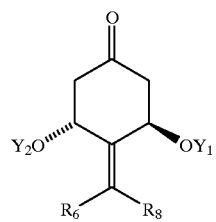

VII

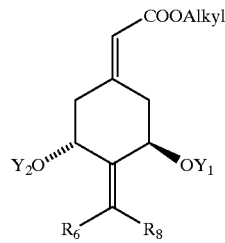

VIII

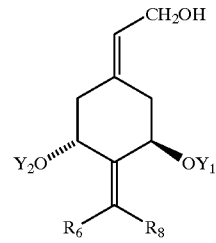

IX

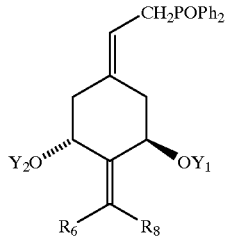

X

This invention also provides a novel synthesis for the production of the end products of structure I.

DETAILED DESCRIPTION OF THE INVENTION

Figure 1:
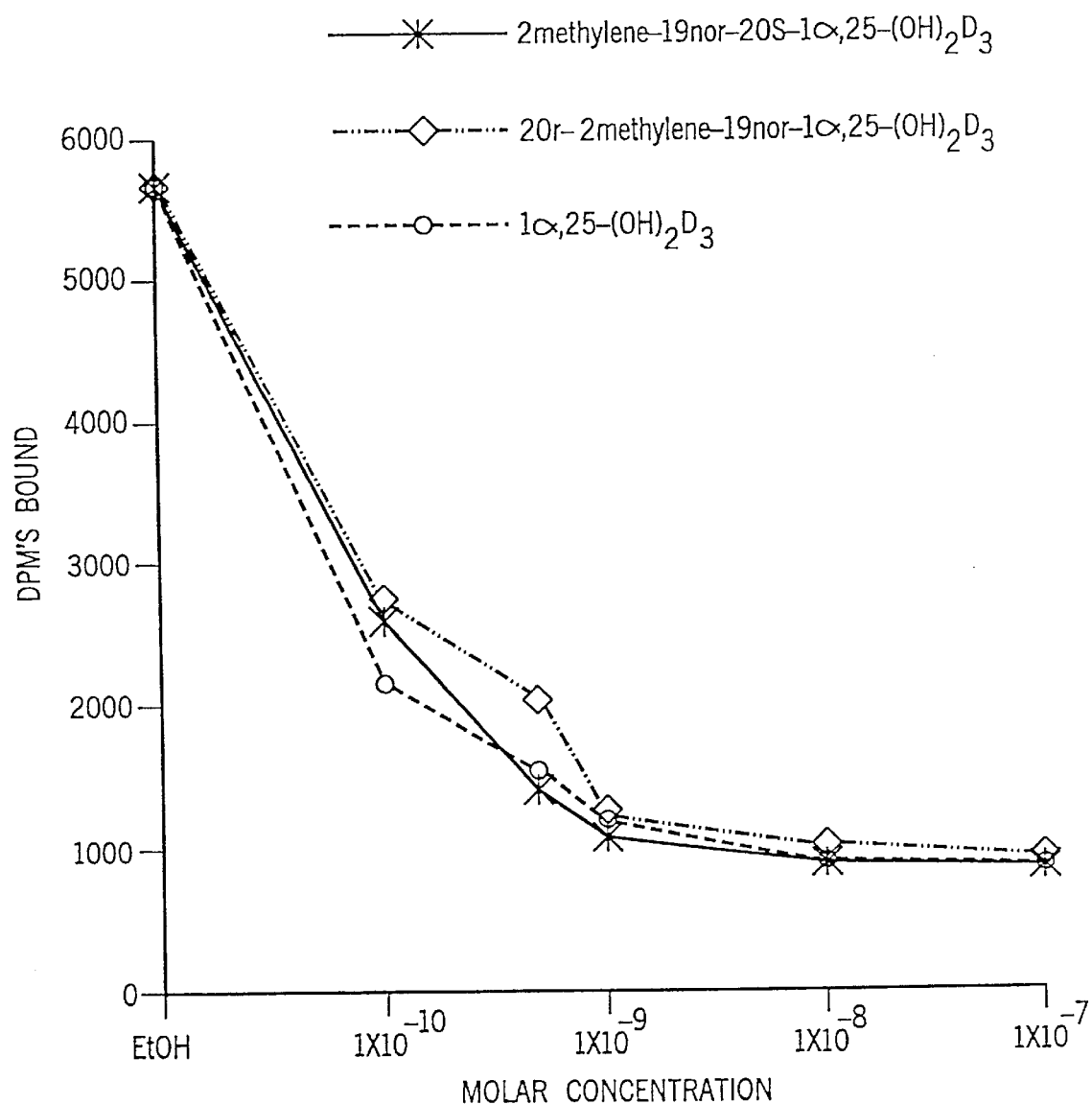
FIG. 1 is a graph illustrating the relative activity of 2-methylene-19-nor-20(S)-1α,25-dihydroxyvitamin $D_3$, 2-methylene-19-nor-1α,25-dihydroxyvitamin $D_3$ and 1α,25-dihydroxyvitamin $D_3$ to compete for binding of [3H]-1,25-$(OH)_2$-$D_3$ to the vitamin D pig intestinal nuclear receptor.

As used in the description and in the claims, the term "hydroxy-protecting group" signifies any group commonly used for the temporary protection of hydroxy functions, such as for example, alkoxycarbonyl, acyl, alkylsilyl or alkylarylsilyl groups (hereinafter referred to simply as "silyl" groups), and alkoxyalkyl groups. Alkoxycarbonyl protecting groups are alkyl-O—CO— groupings such as methoxycarbonyl, ethoxycarbonyl, propoxycarbonyl, isopropoxycarbonyl, butoxycarbonyl, isobutoxycarbonyl, tert-butoxycarbonyl, benzyloxycarbonyl or allyloxycarbonyl. The term "acyl" signifies an alkanoyl group of 1 to 6 carbons, in all of its isomeric forms, or a carboxyalkanoyl group of 1 to 6 carbons, such as an oxalyl, malonyl, succinyl, glutaryl group, or an aromatic acyl group such as benzoyl, or a halo, nitro or alkyl substituted benzoyl group. The word "alkyl" as used in the description or the claims, denotes a straight-chain or branched alkyl radical of 1 to 10 carbons, in all its isomeric forms. Alkoxyalkyl protecting groups are groupings such as methoxymethyl, ethoxymethyl, methoxyethoxymethyl, or tetrahydrofuranyl and tetrahydropyranyl. Preferred silyl-protecting groups are trimethylsilyl, triethylsilyl, t-butyldimethylsilyl, dibutylmethylsilyl, diphenylmethylsilyl, phenyldimethylsilyl, diphenyl-t-butylsilyl and analogous alkylated silyl radicals. The term "aryl" specifies a phenyl-, or an alkyl-, nitro- or halo-substituted phenyl group.

A "protected hydroxy" group is a hydroxy group derivatised or protected by any of the above groups commonly used for the temporary or permanent protection of hydroxy functions, e.g. the silyl, alkoxyalkyl, acyl or alkoxycarbonyl groups, as previously defined. The terms "hydroxyalkyl", "deuteroalkyl" and "fluoroalkyl" refer to an alkyl radical substituted by one or more hydroxy, deuterium or fluoro groups respectively.

It should be noted in this description that the term "24-homo" refers to the addition of one methylene group and the term "24-dihomo" refers to the addition of two methylene groups at the carbon 24 position in the side chain. Likewise, the term "trihomo" refers to the addition of three methylene groups. Also, the term "26,27-dimethyl" refers to the addition of a methyl group at the carbon 26 and 27 positions so that for example $R^3$ and $R^4$ are ethyl groups. Likewise, the term "26,27-diethyl" refers to the addition of an ethyl group at the 26 and 27 positions so that $R^3$ and $R^4$ are propyl groups.

In the following lists of compounds, the particular alkylidene substituent attached at the carbon 2 position should be added to the nomenclature. For example, if a methylene group is the alkylidene substituent, the term "2-methylene" should precede each of the named compounds. If an ethylene group is the alkylidene substituent, the term "2-ethylene" should precede each of the named compounds, and so on. In addition, if the methyl group attached at the carbon 20 position is in its epi or unnaturalconfiguration, the term "20(S)" or "20-epi" should be included in each of the following named compounds. The named compounds could also be of the vitamin $D_2$ type if desired.

Specific and preferred examples of the 2-alkylidene-compounds of structure I when the side chain is unsaturated are:

19-nor-24-homo-1,25-dihydroxy-22-dehydrovitamin $D_3$;
19-nor-24-dihomo-1,25-dihydroxy-22-dehydrovitamin $D_3$;
19-nor-24-trihomo-1,25-dihydroxy-22-dehydrovitamin $D_3$;
19-nor-26,27-dimethyl-24-homo-1,25-dihydroxy-22-dehydrovitamin $D_3$;
19-nor-26,27-dimethyl-24-dihomo-1,25-dihydroxy-22-dehydrovitamin $D_3$;
19-nor-26,27-dimethyl-24-trihomo-1,25-dihydroxy-22-dehydrovitamin $D_3$;
19-nor-26,27-diethyl-24-homo-1,25-dihydroxy-22-dehydrovitamin $D_3$;
19-nor-26,27-diethyl-24-dihomo-1,25-dihydroxy-22-dehydrovitamin $D_3$;
19-nor-26,27-diethyl-24-trihomo-1,25-dihydroxy-22-dehydrovitamin $D_3$;
19-nor-26,27-dipropoyl-24-homo-1,25-dihydroxy-22-dehydrovitamin $D_3$;
19-nor-26,27-dipropyl-24-dihomo-1,25-dihydroxy-22-dehydrovitamin $D_3$;
19-nor-26,27-dipropyl-24-trihomo-1,25-dihydroxy-22-dehydrovitamin $D_3$; and
19-nor-26,27-dimethylene-1-hydroxy-24-dehydrovitamin $D_3$.

A particularly preferred side chain unsaturated compound is:
19-nor-26,27-dimethylene-20(S)-2-methylene-1o-hydroxy-24-dehydrovitamin $D_3$.

Specific and preferred examples of the 2-alkylidene-compounds of structure I when the side chain is saturated are:

19-nor-24-homo-1,25-dihydroxyvitamin $D_3$;
19-nor-24-dihomo-1,25-dihydroxyvitamin $D_3$;
19-nor-24-trihomo-1,25-dihydroxyvitamin $D_3$;
19-nor-26,27-dimethyl-24-homo-1,25-dihydroxyvitamin $D_3$;
19-nor-26,27-dimethyl-24-dihomo-1,25-dihydroxyvitamin $D_3$;
19-nor-26,27-dimethyl-24-trihomo-1,25-dihydroxyvitamin $D_3$;
19-nor-26,27-diethyl-24-homo-1,25-dihydroxyvitamin $D_3$;
19-nor-26,27-diethyl-24-dihomo-1,25-dihydroxyvitamin $D_3$;
19-nor-26,27-diethyl-24-trihomo-1,25-dihydroxyvitanin $D_3$;
19-nor-26,27-dipropyl-24-homo-1,25-dihydroxyvitamin $D_3$;
19-nor-26,27-dipropyl-24-dihomo-1,25-dihydroxyvitamin $D_3$;
19-nor-26,27-dipropyl-24-trihomo-1,25-dihydroxyvitamin $D_3$;
19-nor-26,27-dimethyl-1,25-dihydroxyvitamin $D_3$;
19-nor-26,27-dimethylene-1,25-hydroxyvitamin $D_3$; and
19-nor-26,27-dimethylene-1-hydroxy-25-methoxyvitamin $D_3$.

As noted previously, the above saturated side chain compounds should have the appropriate 2-alkylidene substituent and/or carbon 20 configuration added to the nomenclature. For example, particularly preferred saturated side chain compounds are:

19-nor-26,27-dimethyl-20(S)-2-methylene-1α,25-dihydroxyvitamin $D_3$; which can also be written as 19-nor-26,27-dihomo-20(S)-2-methylene-1α,25-dihydroxyvitamin $D_3$;
19-nor-26,27-dimethylene-20(S)-2-methylene-1α,25-dihydroxyvitamin $D_3$; and
19-nor-26,27-dimethylene-20(S)-2-methylene-1α-hydroxy-25-methoxyvitamin $D_3$.

The preparation of 1α-hydroxy-2-alkylidene-19-nor-vitamin D compounds, particularly 1α-hydroxy-2-methyl-19-nor-vitamin D compounds, having the basic structure I can be accomplished by a common general method, i.e. the condensation of a bicyclic Windaus-Grundmann type ketone II with the allylic phosphine oxide III to the corresponding 2-methylene-19-nor-vitamin D analogs IV followed by deprotection at C-1 and C-3 in the latter compounds:

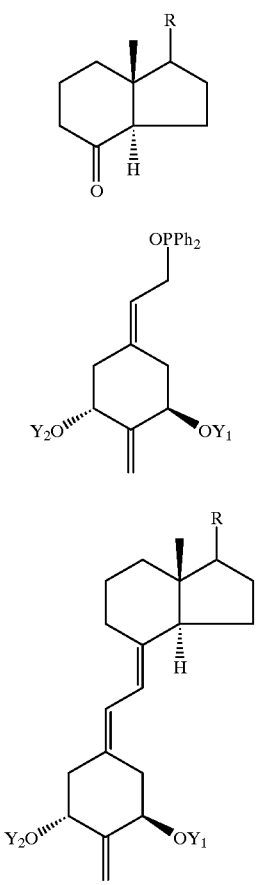

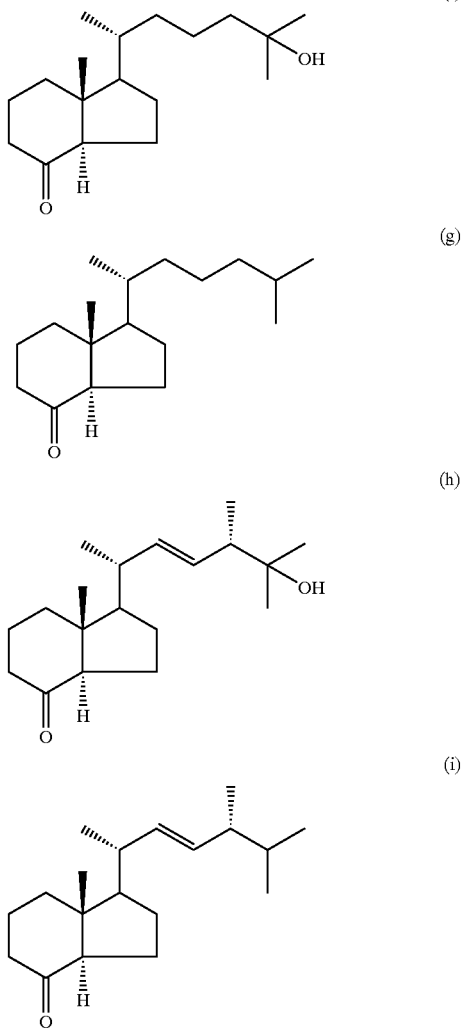

In the structures II, III, and IV groups $Y_1$ and $Y_2$ and R represent groups defined above; $Y_1$ and $Y_2$ are preferably hydroxy-protecting groups, it being also understood that any functionalities in R that might be sensitive, or that interfere with the condensation reaction, be suitable protected as is well-known in the art. The process shown above represents an application of the convergent synthesis concept, which has been applied effectively for the preparation of vitamin D compounds [e.g. Lythgoe et al., J. Chem. Soc. Perkin Trans. I, 590 (1978); Lythgoe, Chem. Soc. Rev. 2, 449 (1983); Toh et al., J. Org. Chem. 48, 1414 (1983); Baggiolini et al., J. Org. Chem. 51, 3098 (1986); Sardina et al., J. Org. Chem. 51, 1264 (1986); J. Org. Chem. 51, 1269 (1986); DeLuca et al., U.S. Pat. No. 5,086,191; DeLuca et al., U.S. Pat. No. 5,536,713].

Hydrindanones of the general structure II are known, or can be prepared by known methods. Specific important examples of such known bicyclic ketones are the structures with the side chains (a), (b), (c) and (d) described above, i.e. 25-hydroxy Grundmann's ketone (f) [Baggiolini et al., J. Org. Chem, 51, 3098 (1986)]; Grundmann's ketone (g) [Inhoffen et al., Chem. Ber. 90, 664 (1957)]; 25-hydroxy Windaus ketone (h) [Baggiolini et al., J. Org. Chem., 51, 3098 (1986)] and Windaus ketone (i) [Windaus et al., Ann., 524, 297 (1936)]:

For the preparation of the required phosphine oxides of general structure III, a new synthetic route has been developed starting from methyl quinicate derivative 1, easily obtained from commercial (1R,3R,4S,5R)-(−)-quinic acid as described by Perlman et al., Tetrahedron Lett. 32, 7663 (1991) and DeLuca et al., U.S. Pat. No. 5,086,191. The overall process of transformation of the starting methyl ester 1 into the desired A-ring synthons, is summarized by the SCHEME I. Thus, the secondary 4-hydroxyl group of 1 was oxidized with $RuO_4$ (a catalytic method with $RuCl_3$ and $NaIO_4$ as co-oxidant). Use of such a strong oxidant was necessary for an effective oxidation process of this very hindered hydroxyl. However, other more commonly used oxidants can also be applied (e.g. pyridinium dichromate), although the reactions usually require much longer time for completion. Second step of the synthesis comprises the Wittig reaction of the sterically hindered 4-keto compound 2 with ylide prepared from methyltriphenylphosphonium bromide and n-butyllithium. Other bases can be also used for the generation of the reactive methylenephosphorane, like t-BuOK, $NaNH_2$, NaH, K/HMPT, $NaN(TMS)_2$, etc. For the preparation of the 4-methylene compound 3 some described modifications of the Wittig process can be used, e.g. reaction of 2 with activated methylenetriphenyl-phosphorane [Corey et al., Tetrahedron Lett. 26, 555 (1985)]. Alternatively, other methods widely used for methylenation of unreactive ketones can be applied, e.g. Wittig-Horner reaction with the PO-ylid obtained from methyldiphenylphosphine oxide upon deprotonation with n-butyllithium [Schosse et al., Chimia 30, 197 (1976)], or reaction of ketone with sodium methylsulfinate [Corey et al., J. Org. Chem. 28, 1128 (1963)] and potassium methylsulfinate [Greene et al., Tetrahedron Lett. 3755 (1976)]. Reduction of the ester 3 with lithium aluminum hydride or other suitable reducing agent (e.g. DIBALH) provided the diol 4 which was subsequently oxidized by sodium periodate to the cyclohexanone derivative 5. The next step of the process comprises the Peterson reaction of the ketone 5 with methyl(trimethylsilyl)acetate. The resulting allylic ester 6 was treated with diisobutylaluminum hydride and the formed allylic alcohol 7 was in turn transformed to the desired A-ring phosphine oxide 8. Conversion of 7 to 8 involved 3 steps, namely, in situ tosylation with n-butyllithium and p-toluenesulfonyl chloride, followed by reaction with diphenylphosphine lithium salt and oxidation with hydrogen peroxide.

Several 2-methylene-19-nor-vitamin D compounds of the general structure IV may be synthesized using the A-ring synthon 8 and the appropriate Windaus-Grundmann ketone II having the desired side chain structure. Thus, for example, Wittig-Horner coupling of the lithium phosphinoxy carbanion generated from 8 and n-butyllithium with the protected 25-hydroxy Grundmann's ketone 9 prepared according to published procedure [Sicinski et al., J. Med. Chem. 37, 3730 (1994)] gave the expected protected vitamin compound 10. This, after deprotection with AG 50W-X4 cation exchange resin afforded 1α,25-dihydroxy-2-methylene-19-nor-vitamin $D_3$ (11).

The C-20 epimerization was accomplished by the analogous coupling of the phosphine oxide 8 with protected 20(S)-25-hydroxy Grundmann's ketone 13 (SCHEME II) and provided 19-nor-vitamin 14 which after hydrolysis of the hydroxy-protecting groups gave 20(S)-1α,25-dihydroxy-2-methylene-19-nor-vitamin $D_3$ (15).

As noted above, other 2-methylene-19-nor-vitamin D analogs may be synthesized by the method disclosed herein. For example, 1α-hydroxy-2-methylene-19-nor-vitamin $D_3$ can be obtained by providing the Grundmann's ketone (g).

This invention is described by the following illustrative examples. In these examples specific products identified by Arabic numerals (e.g. 1, 2, 3, etc) refer to the specific structures so identified in the preceding description and in the SCHEME I and SCHEME II.

EXAMPLE 1

Preparation of 1α,25-Dihydroxy-2-methylene-19-nor-vitamin $D_3$ (11)

Referring first to SCHEME I the starting methyl quinicate derivative 1 was obtained from commercial (−)-quinic acid as described previously [Perlman et al., Tetrahedron Lett. 32, 7663 (1991) and DeLuca et al., U.S. Pat. No. 5,086,191]. 1: mp. 82–82.5° C. (from hexane), $^1$H NMR (CDCl$_3$) 0.098, 0.110, 0.142, and 0.159 (each 3H, each s, 4×SiCH$_3$), 0.896 and 0.911 (9H and 9H, each s, 2×Si-t-Bu), 1.820 (1H, dd, J=13.1, 10.3 Hz), 2.02 (1H, ddd, J=14.3, 4.3, 2.4 Hz), 2.09 (1H, dd, J=14.3, 2.8 Hz), 2.19 (1H, ddd, J=13.1, 4.4, 2.4 Hz), 2.31 (1H, d, J=2.8 Hz, OH), 3.42 (1H, m; after D$_2$O dd, J=8.6, 2.6 Hz), 3.77 (3H, s), 4.12 (1H, m), 4.37 (1H, m), 4.53 (1H, br s, OR).

(a) Oxidation of 4-Hydroxy Group in Methyl Quinicate Derivative 1.

(3R,5R)-3,5-Bis[(tert-butyldimethylsilyl)oxy]-1-hydroxy-4-oxocyclohexanecarboxylic Acid Methyl Ester (2). To a stirred mixture of ruthenium(III) chloride hydrate (434 mg, 2.1 mmol) and sodium periodate (10.8 g, 50.6 mmol) in water (42 mL) was added a solution of methyl quinicate 1 (6.09 g, 14 mmol) in CCl$_4$/CH$_3$CN (1:1, 64 mL). Vigorous stirring was continued for 8 h. Few drops of 2-propanol were added, the mixture was poured into water and extracted with chloroform. The organic extracts were combined, washed with water, dried (MgSO$_4$) and evaporated to give a dark oily residue (ca. 5 g) which was purified by flash chromatography. Elution with hexane/ethyl acetate (8:2) gave pure, oily 4-ketone 2 (3.4 g, 56%): $^1$H NMR (CDCl$_3$) δ 0.054, 0.091, 0.127, and 0.132 (each 3H, each s, 4×SiCH$_3$), 0.908 and 0.913 (9H and 9H, each s, 2×Si-tBu), 2.22 (1H, dd, J=13.2, 11.7 Hz), 2.28 (1H, ~dt, J=14.9, 3.6 Hz), 2.37 (1H, dd, J=14.9, 3.2 Hz), 2.55 (1H, ddd, J=13.2, 6.4, 3.4 Hz), 3.79 (3H, s), 4.41 (1H, t, J~3.5 Hz), 4.64 (1H, s, OH), 5.04 (1H, dd, J=11.7, 6.4 Hz); MS m/z (relative intensity) no M$^+$, 375 (M$^+$-t-Bu, 32), 357 (M$^+$-t-Bu-H$_2$O, 47), 243 (31), 225 (57), 73 (100).

(b) Wittig Reaction of the 4-Ketone 2.

(3R,5R)-3,5-Bis[(tert-butyldimethylsilyl)oxy]-1-hydroxy-4-methylenecyclohexanecarboxylic Acid Methyl Ester (3). To the methyltriphenylphosphonium bromide (2.813 g, 7.88 mmol) in anhydrous THF (32 mL) at 0° C. was added dropwise n-BuLi (2.5 M in hexanes, 6.0 mL, 15 mmol) under argon with stirring. Another portion of MePh$_3$P$^+$Br$^-$ (2.813 g, 7.88 mmol) was then added and the solution was stirred at 0° C. for 10 min and at room temperature for 40 min. The orange-red mixture was again cooled to 0° C. and a solution of 4-ketone 2 (1.558 g, 3.6 mmol) in anhydrous THF (16+2 mL) was syphoned to reaction flask during 20 min. The reaction mixture was stirred at 0° C. for 1 h and and at room temperature for 3 h. The mixture was then carefully poured into brine cont. 1% HCl and extracted with ethyl acetate and benzene. The combined organic extracts were washed with diluted NaHCO$_3$ and brine, dried (MgSO$_4$) and evaporated to give an orange oily residue (ca. 2.6 g) which was purified by flash chromatography. Elution with hexane/ethyl acetate (9:1) gave pure 4-methylene compound 3 as a colorless oil (368 mg, 24%): $^1$H NMR (CDCl$_3$) δ 0.078, 0.083, 0.092, and 0.115 (each 3H, each s, 4×SiCH$_3$), 0.889 and 0.920 (9H and 9H, each s, 2×Si-t-Bu), 1.811 (1H, dd, J=12.6, 11.2 Hz), 2.10 (2H, m), 2.31 (1H, dd, J=12.6, 5.1 Hz), 3.76 (3H, s), 4.69 (1H, t, J=3.1 Hz), 4.78 (1H, m), 4.96 (2H, m; after D$_2$O 1H, br s), 5.17 (1H, t, J=1.9 Hz); MS m/z (relative intensity) no M$^+$, 373 (M$^+$-t-Bu, 57), 355 (M$^+$-t-Bu-H$_2$O, 13), 341 (19), 313 (25), 241 (33), 223 (37), 209 (56), 73 (100).

(c) Reduction of Ester Group in the 4-Methylene Compound 3.

[(3R,5R)-3,5-Bis[(tert-butyldimethylsilyl)oxy]-1-hydroxy-4-methylenecyclohexyl]methanol (4). (i) To a stirred solution of the ester 3 (90 mg, 0.21 mmol) in anhydrous THF (8 mL) lithium aluminum hydride (60 mg, 1.6 mmol) was added at 0° C. under argon. The cooling bath was removed after 1 h and the stirring was continued at 6° C. for 12 h and at room temperature for 6 h. The excess of the reagent was decomposed with saturated aq. Na$_2$SO$_4$, and the mixture was extracted with ethyl acetate and ether, dried (MgSO$_4$) and evaporated. Flash chromatography of the residue with hexane/ethyl acetate (9:1) afforded unreacted substrate (12 mg) and a pure, crystalline diol 4 (35 mg, 48% based on recovered ester 3): $^1$H NMR (CDCl$_3$+D$_2$O) δ 0.079, 0.091, 0.100, and 0.121 (each 3H, each s, 4×SiCH$_3$), 0.895 and 0.927 (9H and 9H, each s, 2×Si-t-Bu), 1.339 (1H, t, J~12 Hz), 1.510 (1H, dd, J=14.3, 2.7 Hz), 2.10 (2H, m), 3.29 and 3.40 (1H and 1H, each d, J=11.0Hz), 4.66 (1H, t, J~2.8 Hz), 4.78 (1H, m), 4.92 (1H, t, J=1.7 Hz), 5.13 (1H, t, J=2.0 Hz); MS m/z (relative intensity) no $M^+$, 345 ($M^+$-t-Bu, 8), 327 ($M^+$-t-Bu-$H_2O$, 22), 213 (28), 195 (11), 73 (100).

(ii) Diisobutylaluminum hydride (1.5 M in toluene, 2.0 mL, 3 mmol) was added to a solution of the ester 3 (215 mg, 0.5 mmol) in anhydrous ether (3 mL) at −78° C. under argon. The mixture was stirred at −78° C. for 3 h and at −24° C. for 1.5 h, diluted with ether (10 mL) and quenched by the slow addition of 2N potassium sodium tartrate. The solution was warmed to room temperature and stirred for 15 min, then poured into brine and extracted with ethyl acetate and ether. The organic extracts were combined, washed with diluted (ca. 1%) HCl, and brine, dried ($MgSO_4$) and evaporated. The crystalline residue was purified by flash chromatography. Elution with hexane/ethyl acetate (9:1) gave crystalline diol 4 (43 mg, 24%).

(d) Cleavage of the Vicinal Diol 4.

(3R,5R)-3,5-Bis[(tert-butyldimethylsilyl)oxy]-4-methylenecyclohexanone (5). Sodium periodate saturated water (2.2 mL) was added to a solution of the diol 4 (146 mg, 0.36 mmol) in methanol (9 mL) at 0° C. The solution was stirred at 0° C. for 1 h, poured into brine and extracted with ether and benzene. The organic extracts were combined, washed with brine, dried ($MgSO_4$) and evaporated. An oily residue was dissolved in hexane (1 mL) and applied on a silica Sep-Pak cartridge. Pure 4-methylenecyclohexanone derivative 5 (110 mg, 82%) was eluted with hexane/ethyl acetate (95:5) as a colorless oil: $^1$H NMR ($CDCl_3$) δ 0.050 and 0.069 (6H and 6H, each s, 4×$SiCH_3$), 0.881 (18H, s, 2×Si-t-Bu), 2.45 (2H, ddd, J=14.2, 6.9, 1.4 Hz), 2.64 (2H, ddd, J=14.2, 4.6, 1.4 Hz), 4.69 (2H, dd, J=6.9,4.6 Hz), 5.16 (2H, s); MS m/z (relative intensity) no $M^+$, 355 ($M^+$-Me, 3), 313 ($M^+$-t-Bu, 100), 73 (76).

(e) Preparation of the Allylic Ester 6.

[(3'R,5'R)-3',5'-Bis[(tert-butyldimethylsilyl)oxy]-4'-methylenecyclohexylidene]acetic Acid Methyl Ester (6). To a solution of diisopropylarnine (37 μL, 0.28 mmol) in anhydrous THF (200 μL) was added n-BuLi (2.5 M in hexanes, 113 μL, 0.28 mmol) under argon at −78° C. with stirring, and methyl(trimethylsilyl)acetate (46 μL, 0.28 mmol) was then added. After 15 min, the keto compound 5 (49 mg, 0.132 mmol) in anhydrous THF (200+80 μL) was added dropwise. The solution was stirred at −78° C. for 2 h and the reaction mixture was quenched with saturated $NH_4Cl$, poured into brine and extracted with ether and benzene. The combined organic extracts were washed with brine, dried ($MgSO_4$) and evaporated. The residue was dissolved in hexane (1 mL) and applied on a silica Sep-Pak cartridge. Elution with hexane and hexane/ethyl acetate (98:2) gave a pure allylic ester 6 (50 mg, 89%) as a colorless oil: $^1$H NMR ($CDCl_3$) δ 0.039, 0.064, and 0.076 (6H, 3H, and 3H, each s, 4×$SiCH_3$), 0.864 and 0.884 (9H and 9H, each s, 2×Si-t-Bu), 2.26 (1H, dd, J=12.8, 7.4 Hz), 2.47 (1H, dd, J=12.8, 4.2 Hz), 2.98 (1H, dd, J=13.3, 4.0 Hz), 3.06 (1H, dd, J=13.3, 6.6 Hz), 3.69 (3H, s), 4.48 (2H, m), 4.99 (2H, s), 5.74 (1H, s); MS m/z (relative intensity) 426 ($M^+$, 2), 411 ($M^+$-Me, 4), 369 ($M^+$-t-Bu, 100), 263 (69).

(f) Reduction of the Allylic Ester 6.

2-[(3'R,5'R)-3',5'-Bis[(tert-butyldimethylsilyl)oxy]-4'-methylenecyclohexylidene]ethanol (7). Diisobutylaluminum hydride (1.5 M in toluene, 1.6 mL, 2.4 mmol) was slowly added to a stirred solution of the allylic ester 6 (143 mg, 0.33 mmol) in toluene/methylene chloride (2:1, 5.7 mL) at −78° C. under argon. Stirring was continued at −78° C. for 1 h and at −46° C. (cyclohexanone/dry ice bath) for 25 min. The mixture was quenched by the slow addition of potassium sodium tartrate (2N, 3 mL), aq. HCl (2N, 3 mL) and $H_2O$ (12 mL), and then diluted with methylene chloride (12 mL) and extracted with ether and benzene. The organic extracts were combined, washed with diluted (ca. 1%) HCl, and brine, dried ($MgSO_4$) and evaporated. The residue was purified by flash chromatography. Elution with hexane/ethyl acetate (9:1) gave crystalline allylic alcohol 7 (130 mg, 97%): $^1$H NMR ($CDCl_3$) 0.038, 0.050, and 0.075 (3H, 3H, and 6H, each s, 4×$SiCH_3$), 0.876 and 0.904 (9H and 9H, each s, 2×Si-t-Bu), 2.12 (1H, dd, J=12.3, 8.8 Hz), 2.23 (1H, dd, J=13.3, 2.7 Hz), 2.45 (1H, dd, J=12.3, 4.8 Hz), 2.51 (1H, dd, J=13.3, 5.4 Hz), 4.04 (1H, m; after $D_2O$ dd, J=12.0, 7.0 Hz), 4.17 (1H, m; after $D_2O$ dd, J=12.0, 7.4 Hz), 4.38 (1H, m), 4.49 (1H, m), 4.95 (1H, br s), 5.05 (1H, t, J=1.7 Hz), 5.69 (1H, ~t, J=7.2 Hz); MS m/z (relative intensity) 398 ($M^+$, 2), 383 ($M^+$-Me, 2), 365 ($M^+$-Me-$H_2O$, 4), 341 ($M^+$-t-Bu, 78), 323 ($M^+$-t-Bu-$H_2O$, 10), 73 (100).

(g) Conversion of the Allylic Alcohol 7 into Phosphine Oxide 8.

[2-[(3'R,5'R)-3',5'-Bis[(tert-butyldimethylsilyl)oxy]-4'-methylenecyclohexylidene]ethyl]diphenylphosphine Oxide (8). To the allylic alcohol 7 (105 mg, 0.263 mmol) in anhydrous THF (2.4 mL) was added n-BuLi (2.5 M in hexanes, 105 μL, 0.263 mmol) under argon at 0° C. Freshly recrystallized tosyl chloride (50.4 mg, 0.264 mmol) was dissolved in anhydrous THF (480 μL) and added to the allylic alcohol-BuLi solution. The mixture was stirred at 0° C. for 5 min and set aside at 0° C. In another dry flask with air replaced by argon, n-BuLi (2.5 M in hexanes, 210 μL, 0.525 mmol) was added to $Ph_2PH$ (93 μL, 0.534 mmol) in anhydrous THF (750 μL) at 0° C. with stirring. The red solution was syphoned under argon pressure to the solution of tosylate until the orange color persisted (ca. ½ of the solution was added). The resulting mixture was stirred an additional 30 min at 0° C., and quenched by addition of $H_2O$ (30 μl). Solvents were evaporated under reduced pressure and the residue was redissolved in methylene chloride (2.4 mL) and stirred with 10% $H_2O_2$ at 0° C. for 1 h. The organic layer was separated, washed with cold aq. sodium sulfite and $H_2O$, dried ($MgSO_4$) and evaporated. The residue was subjected to flash chromatography. Elution with benzene/ethyl acetate (6:4) gave semicrystalline phosphine oxide 8 (134 mg, 87%): $^1$H NMR ($CDCl_3$) δ 0.002, 0.011, and 0.019 (3H, 3H, and 6H, each s, 4×$SiCH_3$), 0.855 and 0.860 (9H and 9H, each s, 2×Si-t-Bu), 2.0–2.1 (3H, br m), 2.34 (1H, m), 3.08 (1H, m), 3.19 (1H, m), 4.34 (2H, m), 4.90 and 4.94 (1H and 1H, each s,), 5.35 (1H, ~q, J=7.4 Hz), 7.46 (4H, m), 7.52 (2H, m), 7.72 (4H, m); MS m/z (relative intensity) no $M^+$, 581 ($M^+$-1, 1), 567 ($M^+$-Me, 3), 525 ($M^+$-t-Bu, 100), 450 (10), 393 (48).

(h) Wittig-Horner Coupling of Protected 25-Hydroxy Grundmann's Ketone 9 with the Phosphine Oxide 8.

1α,25-Dihydroxy-2-methylene-19-nor-vitamin $D_3$ (11). To a solution of phosphine oxide 8 (33.1 mg, 56.8 μmol) in anhydrous THF (450 μL) at 0° C. was slowly added n-BuLi (2.5 M in hexanes, 23 μL, 57.5 μmol) under argon with stirring. The solution turned deep orange. The mixture was cooled to −78° C. and a precooled (−78° C.) solution of protected hydroxy ketone 9 (9.0 mg, 22.8 μmol), prepared according to published procedure [Sicinski et al., J. Med. Chem. 37, 3730 (1994)], in anhydrous THF (200+100 μL) was slowly added. The mixture was stirred under argon at −78° C. for 1 h and at 0° C. for 18 h. Ethyl acetate was added, and the organic phase was washed with brine, dried ($MgSO_4$) and evaporated. The residue was dissolved in hexane and applied on a silica Sep-Pak cartridge, and washed with hexane/ethyl acetate (99:1, 20 mL) to give 19-nor-vitamin derivative 10 (13.5 mg, 78%). The Sep-Pak was then washed with hexane/ethyl acetate (96:4, 10 mL) to recover some unchanged C,D-ring ketone 9 (2 mg), and with ethyl acetate (10 mL) to recover diphenylphosphine oxide (20 mg). For analytical puipose a sample of protected vitamin 10 was further purified by HPLC (6.2 mm×25 cm Zorbax-Sil column, 4 mL/min) using hexane/ethyl acetate (99.9:0.1) solvent system. Pure compound 10 was eluted at $R_V$ 26 mL as a colorless oil: UV (in hexane) $\lambda_{max}$ 244, 253, 263 nm; $^1$H NMR (CDCl$_3$) δ 0.025, 0.049, 0.066, and 0.080 (each 3H, each s, 4×SiCH$_3$), 0.546 (3H, s, 18-H$_3$), 0.565 (6H, q, J=7.9 Hz, 3×SiCH$_2$), 0.864 and 0.896 (9H and 9H, each s, 2×Si-t-Bu), 0.931 (3H, d, J=6.0 Hz, 21-H$_3$), 0.947 (9H, t, J=7.9 Hz, 3×SiCH$_2$CH$_3$), 1.188 (6H, s, 26- and 27-H$_3$), 2.00 (2H, m), 2.18 (1H, dd, J=12.5, 8.5 Hz, 4β-H), 2.33 (1H, dd, J=13.1, 2.9 Hz, 10β-H), 2.46 (1H, dd, J=12.5, 4.5 Hz, 4α-H), 2.52 (1H, dd, J=13.1, 5.8 Hz, 10α-H), 2.82 (1H, br d, J=12 Hz, 9β-H), 4.43 (2H, m, 1β- and 3α-H), 4.92 and 4.97 (1H and 1H, each s, =CH$_2$), 5.84 and 6.22 (1H and 1H, each d, J=11.0 Hz, 7- and 6-H); MS m/z (relative intensity) 758 (M$^+$, 17), 729 (M$^+$-Et, 6), 701 (M$^+$-t-Bu, 4), 626 (100), 494 (23), 366 (50), 73 (92).

Protected vitamin 10 (4.3 mg) was dissolved in benzene (150 μL) and the resin (AG 50W-X4, 60 mg; prewashed with methanol) in methanol (800 μL) was added. The mixture was stirred at room temperature under argon for 17 h, diluted with ethyl acetate/ether (1:1, 4 mL) and decanted. The resin was washed with ether (8 mL) and the combined organic phases washed with brine and saturated NaHCO$_3$, dried (MgSO$_4$) and evaporated. The residue was purified by HPLC (6.2 mm×25 cm Zorbax-Sil column, 4 mL/min) using hexane/2-propanol (9:1) solvent system. Analytically pure 2-methylene-19-nor-vitamin 11 (2.3 mg, 97%) was collected at $R_V$ 29 mL (1α,25-dihydroxyvitamin D$_3$ was eluted at $R_v$ 52 mL in the same system) as a white solid: UV (in EtOH) $\lambda_{max}$ 243.5, 252, 262.5 nm; $^1$H NMR (CDCl$_3$) δ 0.552 (3H, s, 18-H$_3$), 0.941 (3H, d, J=6.4 Hz, 21-H$_3$), 1.222 (6H, s, 26- and 27-H$_3$), 2.01 (2H, m), 2.27–2.36 (2H, m), 2.58 (1H, m), 2.80–2.88 (2H, m, 1β- and 3α-H), 5.10 and 5.11 (1H and 1H, each s, =CH$_2$), 5.89 and 6.37 (1H and 1H, each d, J=11.3 Hz, 7- and 6-H); MS m/z (relative intensity) 416 (M$^+$, 83), 398 (25), 384 (31), 380 (14), 351 (20), 313 (100).

EXAMPLE 2

Preparation of 20(S)-1α,25-dihydroxy-2-methylene-19-nor-vitamin D$_3$ (15).

SCHEME II illustrates the preparation of protected 20(S)-25-hydroxy Grundmann's ketone 13, and its coupling with phosphine oxide 8 (obtained as described in Example 1).

(a) Silylation of Hydroxy Ketone 12.

20(S)-25-[(Triethylsilyl)oxy]-des-A,B-cholestan-8-one (13). A solution of the ketone 12 (Tetrionics, Inc.; 56 mg, 0.2 mmol) and imidazole (65 mg, 0.95 mmol) in anhydrous DMF (1.2 mL) was treated with triethylsilyl chloride (95 μL, 0.56 mmol), and the mixture was stirred at room temperature under argon for 4 h. Ethyl acetate was added and water, and the organic layer was separated. The ethyl acetate layer was washed with water and brine, dried (MgSO$_4$) and evaporated. The residue was passed through a silica Sep-Pak cartridge in hexane/ethyl acetate (9:1), and after evaporation, purified by HPLC (9.4 mm×25 cm Zorbax-Sil column, 4 mL/min) using hexane/ethyl acetate (9:1) solvent system. Pure protected hydroxy ketone 13 (55 mg, 70%) was eluted at $R_V$ 35 mL as a colorless oil: $^1$H NMR (CDCl$_3$) δ 0.566 (6H, q, J=7.9 Hz, 3×SiCH$_2$), 0.638 (3H, s, 18-H$_3$), 0.859 (3H, d, J=6.0 Hz, 21-H$_3$), 0.947 (9H, t, J=7.9 Hz, 3×SiCH$_2$CH$_3$), 1.196 (6H, s, 26- and 27-H$_3$), 2.45 (1H, dd, J=11.4, 7.5 Hz, 14α-H).

(b) Wittig-Horner Coupling of Protected 20(S)-25-Hydroxy Grundmann's Ketone 13 with the Phosphine Oxide 8.

20(S)-1α,25-Dihydroxy-2-methylene-19-nor-vitamin D$_3$ (15). To a solution of phosphine oxide 8 (15.8 mg, 27.1 μmol) in anhydrous THF (200 μL) at 0° C. was slowly added n-BuLi (2.5 M in hexanes, 11 μL, 27.5 μmol) under argon with stirring. The solution turned deep orange. The mixture was cooled to −78° C. and a precooled (−78° C.) solution of protected hydroxy ketone 13 (8.0 mg, 20.3 pmol) in anhydrous THF (100 μL) was slowly added. The mixture was stirred under argon at −78° C. for 1 h and at 0° C. for 18 h. Ethyl acetate was added, and the organic phase was washed with brine, dried (MgSO$_4$) and evaporated. The residue was dissolved in hexane and applied on a silica Sep-Pak cartridge, and washed with with hexane/ethyl acetate (99.5:0.5, 20 mL) to give 19-nor-vitamin derivative 14 (7 mg, 45%) as a colorless oil. The Sep-Pak was then washed with hexane/ethyl acetate (96:4, 10 mL) to recover some unchanged C,D-ring ketone 13 (4 mg), and with ethyl acetate (10 mL) to recover diphenylphosphine oxide (9 mg). For analytical purpose a sample of protected vitamin 14 was further purified by HPLC (6.2 mm×25 cm Zorbax-Sil column, 4 mL/min) using hexane/ethyl acetate (99.9:0.1) solvent system.

14: UV (in hexane) $\lambda_{max}$ 244, 253.5, 263 nm; $^1$H NMR (CDCl$_3$) δ 0.026, 0.049, 0.066, and 0.080 (each 3H, each s, 4×SiCH$_3$), 0.541 (3H, s, 18-H$_3$), 0.564 (6H, q, J=7.9 Hz, 3×SiCH$_2$), 0.848 (3H, d, J=6.5 Hz, 21-H$_3$), 0.864 and 0.896 (9H and 9H, each s, 2×Si-t-Bu), 0.945 (9H, t, J=7.9 Hz, 3×SiCH$_2$CH$_3$), 1.188 (6H, s, 26- and 27-H$_3$), 2.15–2.35 (4H, br m), 2.43–2.53 (3H, br m), 2.82 (1H, br d, J=12.9 Hz, 9β-H), 4.42 (2H, m, 1β- and 3α-H), 4.92 and 4.97 (1H and 1H, each s, =CH$_2$), 5.84 and 6.22 (1H and 1H, each d, J=11.1 Hz, 7- and 6-H); MS m/z (relative intensity) 758 (M$^+$, 33), 729 (M$^+$-Et, 7), 701 (M$^+$-t-Bu, 5), 626 (100), 494 (25), 366 (52), 75 (82), 73 (69).

Protected vitamin 14 (5.0 mg) was dissolved in benzene (160 μL) and the resin (AG 50W-X4, 70 mg; prewashed with methanol) in methanol (900 μL) was added. The mixture was stirred at room temperature under argon for 19 h, diluted with ethyl acetate/ether (1:1, 4 mL) and decanted. The resin was washed with ether (8 mL) and the combined organic phases washed with brine and saturated NaHCO$_3$, dried (MgSO$_4$) and evaporated. The residue was purified by HPLC (6.2 mm×25 cm Zorbax-Sil column, 4 mL/min) using hexane/2-propanol (9:1) solvent system. Analytically pure 2-methylene-19-nor-vitamin 15 (2.6 mg, 95%) was collected at $R_V$ 28 mL [(20R)-analog was eluted at $R_v$ 29 mL and 1α,25-dihydroxyvitamin D$_3$ at $R_v$ 52 mL in the same system] as a white solid: UV (in EtOH) $\lambda_{max}$ 243.5, 252.5, 262.5 nm; $^1$H NMR (CDCl$_3$) δ 0.551 (3H, s, 18-H$_3$), 0.858 (3H, d, J=6.6 Hz, 21-H$_3$), 1.215 (6H, s, 26- and 27-H$_3$), 1.95–2.04 (2H, m), 2.27–2.35 (2H, m), 2.58 (1H, dd, J=13.3, 3.7 Hz), 2.80–2.87 (2H, m), 4.49 (2H, m, 1β- and 3α-H), 5.09 and 5.11 (1H and 1H, each s, =CH$_2$), 5.89 and 6.36 (1H and 1H, each d, J=11.3 Hz, 7- and 6-H); MS m/z (relative intensity) 416 (M$^+$, 100), 398 (26), 380 (13), 366 (21), 313 (31).

BIOLOGICAL ACTIVITY OF 2-METHYLENE-SUBSTITUTED 19-NOR-1,25-(OH)$_2$D$_3$ COMPOUNDS AND THEIR 20(S)-ISOMERS

The introduction of a methylene group to the 2-position of 19-nor-1,25-(OH)$_2$D$_3$ or its 20(S)-isomer had little or no effect on binding to the porcine intestinal vitamin D receptor. All compounds bound equally well to the porcine receptor including the standard 1,25-(OH)$_2$D$_3$ (FIG. 1). It might be expected from these results that all of these compounds would have equivalent biological activity. Surprisingly, however, the 2 methylene substitutions produced highly selective analogs with their primary action on bone. When given for 7 days in a chronic mode, the most potent compound tested was the 2-methylene-19-nor-20(S)-1,25-(OH)$_2$D$_3$ (Table 1). When given at 130 pmol/day, its activity on bone calcium mobilization (serum calcium) was of the order of at least 10 and possible 100–1,000 times more than that of the native hormone. Under identical conditions, twice the dose of 1,25-(OH)$_2$D$_3$ gave a serum calcium value of 13.8 mg/100 ml of serum calcium at the 130 pmol dose. When given at 260 pmol/day, it produced the astounding value of 14 mg/100 ml of serum calcium at the expense of bone. To show its selectivity, this compound produced no significant change in intestinal calcium transport at either the 130 or 260 pmol dose, while 1,25-(OH)$_2$D$_3$ produced the expected elevation of intestinal calcium transport at the only dose tested, i.e. 260 pmol/day. The 2-methylene-19-nor-1,25-(OH)$_2$D$_3$ also had extremely strong bone calcium mobilization at both dose levels but also showed no intestinal calcium transport activity. The bone calcium mobilization activity of this compound is likely to be 10–100 times that of 1,25-(OH)$_2$D$_3$. These results illustrate that the 2-methylene and the 20(S)-2-methylene derivatives of 19-nor-1,25-(OH)$_2$D$_3$ are selective for the mobilization of calcium from bone. Table 2 illustrates the response of both intestine and serum calcium to a single large dose of the various compounds; again, supporting the conclusions derived from Table 1.

Figure 2:
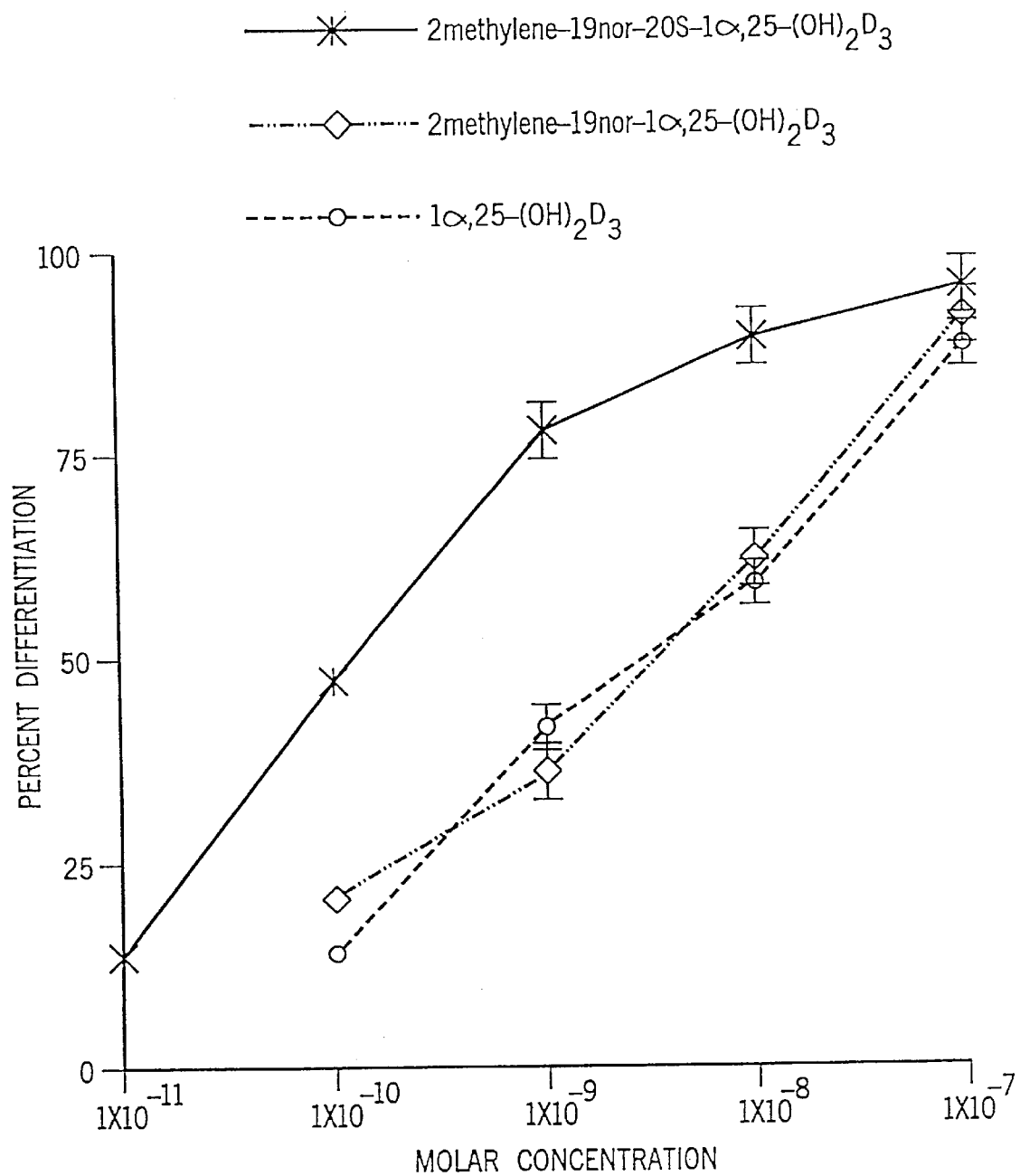
FIG. 2 is a graph illustrating the percent HL-60 cell differentiation as a function of the concentration of 2-methylene-19-nor-20(S)-1α,25-dihydroxyvitamin $D_3$, 2-methylene-19-nor-1α,25-dihydroxyvitamin $D_3$ and 1α,25-dihydroxyvitamin $D_3$.

The results in FIG. 2 illustrate that 2-methylene-19-nor-20(S)-1,25-(OH)$_2$D$_3$ is extremely potent in inducing differentiation of HL-60 cells to the moncyte. The 2-methylene-19-nor compound had activity similar to 1,25-(OH)$_2$D$_3$. These results illustrate the potential of the 2-methylene-19-nor-20(S)-1,25-(OH)$_2$D$_3$ and 2-methylene-19-nor-1,25-(OH)$_2$D$_3$ compounds as anti-cancer agents, especially against leukemia, colon cancer, breast cancer and prostate cancer, or as agents in the treatment of psoriasis.

Competitve binding of the analogs to the porcine intestinal receptor was carried out by the method described by Dame et al (Biochemistry 25, 4523–4534, 1986).

The differentiation of HL-60 promyelocytic into monocytes was determined as described by Ostrem et al (J. Biol. Chem. 262, 14164–14171, 1987).

TABLE 1

Response of Intestinal Calcium Transport and Serum Calcium (Bone Calcium Mobilization) Activity to Chronic Doses of 2-Methylene Derivatives of 19-Nor-1,25-(OH)$_2$D$_3$ and its 20(S) Isomers

| Group | Dose (pmol/day/7 days) | Intestinal Calcium Transport (S/M) | Serum Calcium (mg/100 ml) |
|---|---|---|---|
| Vitamin D Deficient | Vehicle | 5.5 ± 0.2 | 5.1 ± 0.16 |
| 1,25-(OH)$_2$D$_3$ Treated | 260 | 6.2 ± 0.4 | 7.2 ± 0.5 |
| 2-Methylene-19-Nor-1,25-(OH)$_2$D$_3$ | 130 | 5.3 ± 0.4 | 9.9 ± 0.2 |
|  | 260 | 4.9 ± 0.6 | 9.6 ± 0.3 |
| 2-Methylene-19-Nor-20(S)-1,25-(OH)$_2$D$_3$ | 130 | 5.7 ± 0.8 | 13.8 ± 0.5 |
|  | 260 | 4.6 ± 0.7 | 14.4 ± 0.6 |

Male weanling rats were obtained from Sprague Dawley Co. (Indianapolis, Ind.) and fed a 0.47% calcium, 0.3% phosphorus vitamin D-deficient diet for 1 week and then given the same diet containing 0.02% calcium, 0.3% phosphorus for 2 weeks. During the last week they were given the indicated dose of compound by intraperitoneal injection in 0.1 ml 95% propylene glycol and 5% ethanol each day for 7 days. The control animals received only the 0.1 ml of 95% propylene glycol, 5% ethanol. Twenty-four hours after the last dose, the rats were sacrificed and intestinal calcium transport was determined by everted sac technique as previously described and serum calcium determined by atomic absorption spectrometry on a model 3110 Perkin Elmer instrument (Norwalk, Conn.). There were 5 rats per group and the values represent mean±SEM.

TABLE 2

Response of Intestinal Calcium Transport and Serum Calcium (Bone Calcium Mobilization) Activity to a Single Dose of the 2-Methylene-Derivatives of 19-Nor-1,25-(OH)$_2$D$_3$ and its 20(S) Isomers

| Group | Intestinal Calcium Transport (S/M) | Serum Calcium (mg/100 ml) |
|---|---|---|
| -D Control | 4.2 ± 0.3 | 4.7 ± 0.1 |
| 1,25-(OH)$_2$D$_3$ | 5.8 ± 0.3 | 5.7 ± 0.2 |
| 2-Methylene-19-Nor-1,25-(OH)$_2$D$_3$ | 5.3 ± 0.5 | 6.4 ± 0.1 |
| 2-Methylene-19-Nor-20(S)-1,25-(OH)$_2$D$_3$ | 5.5 ± 0.6 | 8.0 ± 0.1 |

Male Holtzman strain weanling rats were obtained from the Sprague Dawley Co. (Indianapolis, Ind.) and fed the 0.47% calcium, 0.3% phosphorus diet described by Suda et al. (J. Nutr. 100, 1049–1052, 1970) for 1 week and then fed the same diet containing 0.02% calcium and 0.3% phosphorus for 2 additional weeks. At this point, they received a single intrajugular injection of the indicated dose dissolved in 0.1 ml of 95% propylene glycol/5% ethanol. Twenty-four hours later they were sacrificed and intestinal calcium transport and serum calcium were determined as described in Table 1. The dose of the compounds was 650 pmol and there were 5 animals per group. The data are expressed as mean±SEM.

EXAMPLE 3

Preparation of 20(S)-1α,25-Dihydroxy-2-methylene-26,27-dihomo-19-norvitamin D$_3$ (35). Reference is made to SCHEME III.

20(S)-25-[(Triethylsilyl)oxy]-des-A,B-26,27-dihomocholestan-8-one (32). To a solution of 20(S)-25-hydroxy Grundmann's ketone analog 31 (Tetrionics, Madison, Wis.; 18.5 mg, 0.06 mmol) in anhydrous CH$_2$Cl$_2$ (60 μL) was added 2,6-lutidine (17.4 μL, 0.15 mmol) and triethylsilyl trifluoromethanesulfonate (20.3 μL, 0.09 mmol). The mixture was stirred at room temperature under argon for 1 h. Benzene was added and water, and the organic layer was separated, washed with sat. CuSO$_4$ and water, dried (MgSO$_4$) and evaporated. The oily residue was redissolved in hexane and applied on a silica Sep-Pak cartridge (2 g). Elution with hexane (10 mL) gave a small quantity of less polar compounds; further elution with hexane/ethyl acetate (9:1) provided the silylated ketone. Final purification was achieved by HPLC (10-mm×25-cm Zorbax-Sil column, 4 mL/min) using hexane/ethyl acetate (95:5) solvent system. Pure protected hydroxy ketone 32 (16.7 mg, 66%) was eluted at R$_v$ 37 mL as a colorless oil: $^1$H NMR (CDCl$_3$) 0.573 (6H, q, J=7.9 Hz, 3×SiCH$_2$), 0.639 (3H, s, 18-H$_3$), 0.825 (6H, t, J=7.5 Hz, 26- and 27-CH$_3$), 0.861 (3H, d, J=6.1 Hz, 21-H$_3$), 0.949 (9H, t, J=7.9 Hz, 3×SiCH$_2$CH$_3$), 2.45 (1H, dd, J=11.4, 7.6 Hz, 14α-H).

20(S)-1α,25-Dihydroxy-2-methylene-26,27-dihomo-19-norvitamin $D_3$ (35). To a solution of phosphine oxide 33 (9.1 mg, 15.6 μmol) in anhydrous THF (150 μL) at 0° C. was slowly added n-BuLi (2.5 M in hexanes, 7 μL, 17.5 μmol) under argon with stirring. The solution turned deep orange. It was stirred for 10 min at 0° C., then cooled to −78° C. and a precooled (−78° C.) solution of protected hydroxy ketone 32 (16.5 mg, 39.0 μmol) in anhydrous THF (300+100 μL) was slowly added. The mixture was stirred under argon at −78° C. for 1.5 h and at 0° C. for 19 h. Water and ethyl acetate were added, and the organic phase was washed with brine, dried ($MgSO_4$) and evaporated. The residue was dissolved in hexane and applied on a silica Sep-Pak cartridge, and washed with hexane/ethyl acetate (99.7:0.3, 20 mL) to give slightly impure 19-norvitamin derivative 34 (ca. 4 mg). The Sep-Pak was then washed with hexane/ethyl acetate (96:4, 10 mL) to recover some unchanged C,D-ring ketone (contaminated with 14β-isomer), and with ethyl acetate (10 mL) to recover diphenylphosphine oxide 33 (ca. 6 mg) that was subsequently purified by HPLC (10-mm× 25-cm Zorbax-Sil colunm, 4 mL/min) using hexane/2-propanol (9:1) solvent system; pure compound 33 (5.1 mg) was eluted at $R_v$ 36 mL. The protected vitamin 34 was further purified by HPLC (6.2-mm×25-cm Zorbax-Sil column, 4 mL/min) using hexane/ethyl acetate (99.9:0.1) solvent system. Pure compound 34 (3.6 mg, 67% yield considering the recovery of unreacted 33) was eluted at $R_v$ 19 mL as a colorless oil: UV (in hexane) $_{max}$ 244.0, 252.5, 262.5 nm; $^1$H NMR ($CDCl_3$) 0.026, 0.048, 0.066, and 0.079 (each 3H, each s, 4×$SiCH_3$), 0.544 (3H, s, 18-$H_3$), 0.570 (6H, q, J=7.9 Hz, 3×$SiCH_2$), 0.821 (6H, t, J=7.5 Hz, 26- and 27-$CH_3$), 0.849 (3H, d, J=6.7 Hz, 21-$H_3$), 0.864 and 0.896 (9H and 9H, each s, 2×Si-t-Bu), 0.946 (9H, t, J=7.9 Hz, 3×$SiCH_2CH_3$), 1.99 (2H, m), 2.18 (1H, dd, J=12.6, 8.2 Hz, 4β-H), 2.34 (1H, dd, J=13.0, 2.9 Hz, 10β-H), 2.46 (1H, dd, J=12.6, 4.3 Hz, 4 -H), 2.51 (1H, dd, J=13.0, 6.2 Hz, 10 -H), 2.82 (1H, br d, J=12 Hz, 9β-H), 4.43 (2H, m, 1β- and 3 -H), 4.92 and 4.97 (1H and 1H, each s, =$CH_2$), 5.84 and 6.22 (1H and 1H, each d, J=11.2 Hz, 7- and 6-H); MS m/z (relative intensity) 786 ($M^+$, 15), 757 ($M^+$-Et, 22), 729 ($M^+$-t-Bu, 5), 654 (100), 522 (15), 366 (43), 201 (31).

Protected vitamin 34 (3.5 mg) was dissolved in benzene (150 μL) and the resin (AG 50W-X4, 40 mg; prewashed with methanol) in methanol (550 μL) was added. The mixture was stirred at room temperature under argon for 14 h, diluted with ethyl acetate/ether (1:1, 4 mL) and decanted. The resin was washed with ether (8 mL) and the combined organic phases washed with brine and saturated $NaHCO_3$, dried ($MgSO_4$) and evaporated. The residue was purified by HPLC (6.2-mm×25-cm Zorbax-Sil column, 4 mL/min) using hexane/2-propanol (9:1) solvent system. Analytically pure 2-methylene-19-norvitamin 35 (1.22 mg, 62%) was collected at $R_v$ 21 mL as a white solid: UV (in EtOH) $λ_{max}$ 243.5, 252.0, 262.0 nm; $^1$H NMR ($CDCl_3$) δ 0.550 (3H, s, 18-$H_3$), 0.855 (3H, d, J=6.8 Hz, 21-$H_3$), 0.860 (6H, t, J=7.5 Hz, 26- and 27-$CH_3$), 2.00 (3H, m), 2.30 (1H, dd, J=13.3, 8.6 Hz, 10α-H), 2.33 (1H, dd, J=13.3, 6.3 Hz, 4β-H), 2.58 (1H, dd, J=13.3, 3.9 Hz, 4α-H), 2.82 (1H, br d, J=12 Hz, 9β-H), 2.85 (1H, dd, J=13.3, 4.7 Hz, 10β-H), 4.48 (2H, m, 1β- and 3α-H), 5.09 and 5.11 (1H and 1H, each s, =$CH_2$), 5.89 and 6.36 (1H and 1H, each d, J=11.3 Hz, 7- and 6-H); MS m/z (relative intensity) 444 ($M^+$, 100), 426 (35), 408 (11), 397 (19), 379 (32), 341 (31), 287 (32), 273 (43), 269 (28), 251 (22); exact mass calcd for $C_{29}H_{48}O_3$ 444.3603, found 444.3602.

BIOLOGICAL ACTIVITY OF 20(S)-1α,25-DIHYDROXY-2-METHYLENE-26,27-DIHOMO-19-NORVITAMIN $D_3$ (35)

Competitive binding of the analogs to the porcine intestinal receptor was carried out by the method described by Dame et al (Biochemistry 25, 4523–4534, 1986).

The differentiation of HL-60 promyleocytic into monocytes was determined as described by Ostrem et al (J. Biol. Chem. 262, 14164–14171, 1987).

TABLE 3

VDR Binding Properties[a] and HL-60 Differentiating Activities[b] of 2-Substituted Analogs of 20(S)-1α,25-Dihydroxy-26,27-dihomo-19-norvitamin $D_3$

| Compound | Compd. no. | VDR Binding $ED_{50}$ (M) | Binding ratio | HL-60 Differentiation $ED_{50}$ (M) | Activity ratio |
|---|---|---|---|---|---|
| 1α,25-$(OH)_2D_3$ | | 8.7 × $10^{-10}$ | 1 | 4.0 × $10^{-9}$ | 1 |
| 2-methylene-26,27-dihomo-19-nor-20(S)-1α,25-$(OH)_2D_3$ | 35 | 4.3 × $10^{-9}$ | 4.9 | 2.6 × $10^{-11}$ | 0.01 |

[a]Competitive binding of 1α,25-$(OH)_2D_3$ and the synthesized vitamin D analogs to the porcine intestinal vitamin D receptor. The experiments were carried out in triplicate on two different occasions. The $ED_{50}$ values are derived from dose-response curves and represent the analog concentration required for 50% displacement of the radiolabeled 1α,25-$(OH)_2D_3$ from the receptor protein. Binding ratio is the ratio of the analog average $ED_{50}$ to the $ED_{50}$ for 1α,25-$(OH)_2D_3$.
[b]Induction of differentiation of HL-60 promyelocytes to monocytes by 1α,25-$(OH)_2D_3$ and the synthesized vitamin D analogs. Differentiation state was determined by measuring the percentage of cells reducing nitro blue tetrazolium (NBT). The experiment was repeated three times. The values $ED_{50}$ are derived from dose-response curves and represent the analog concentration capable of inducing 50% maturation. Differentiation activity radio is the ratio of the analog average $ED_{50}$ to the $ED_{50}$ for 1α,25-$(OH)_2D_3$.

TABLE 4

Support of Intestinal Calcium Transport and Bone Calcium Mobilization by 2-Substituted Analogs of 20(S)-1α,25-Dihydroxy-26,27-dihomo-19-norvitamin $D_3$ in Vitamin D-Deficient Rats on a Low-Calcium Diet[a]

| Compound | Compd. no. | Amount (pmol) | Ca Transport S/M (mean ± SEM) | Serum Ca (mean ± SEM) |
|---|---|---|---|---|
| none (control) | | 0 | 2.7 ± 0.3[b] | 4.7 ± 0.2[b] |
| 1α,25-$(OH)_2D_3$ | | 260 | 7.2 ± 0.6[c] | 5.6 ± 0.2[c] |
| 2-methylene-26,27-dihomo-19-nor-20(S)-1α,25-$(OH)_2D_3$ | 35 | 15 | 4.0 ± 0.4[d1] | 5.3 ± 0.1[d1] |
| | | 32 | 8.2 ± 0.6[d2] | 7.3 ± 0.4[d2] |

[a]Weanling male rats were maintained on a 0.47% Ca diet for 1 week and then switched to a low-calcium diet containing 0.02% Ca for an additional 3 weeks. During the last week, they were dosed daily with the appropriate vitamin D compound for 7 consecutive days. All doses were administered intraperitoneally in 0.1 ml propylene glycol/ethanol (95:5). Controls received the vehicle. Determinations were made 24 h after the last dose. There were at least 6 rats per group. Statistical analysis was done by Student's t-test. Statistical data: serosal/mucosal (S/M), b from c and $d^2$, p<0.001, b from $d^1$, NS; serum calcium, b from c, p<0.05, b from $d^1$, NS, b from $d^2$, p=0.005.

EXAMPLE 4

Preparation of 20(S)-26,27-dimethylene-1α-hydroxy-2-methylene-24-dehydro-19-norvitamin $D_3$ (45); 20(S)-26,27-dimethylene-1α-hydroxy-25-methoxy-2-methylene-19-norvitamin $D_3$ (46); and 20(S)-1α,25-dihydroxy-26,27-dimethylene-2-methylene-19-norvitamin $D_3$ (47).

Reference is made to SCHEME IV.

20(S)-25-[(Triethylsilyl)oxy]-des-A,B-26,27-dimethylene-cholestan-8-one (42). To a solution of 20(S)-

25-hydroxy Grundmann's ketone analog 41 (Tetrionics, Madison, Wis.; 15.0 mg, 0.049 mmol) in anhydrous $CH_2Cl_2$ (50 μL) was added 2,6-lutidine (15 μL, 0.129 mmol) and triethylsilyl trifluoromethanesulfonate (17.0 μL, 0.075 mmol). The mixture was stirred at room temperature under argon for 1 h. Benzene was added and water, and the organic layer was separated, washed with sat. $CuSO_4$ and water, dried ($MgSO_4$) and evaporated. The oily residue was redissolved in hexane and applied on a silica Sep-Pak cartridge (2 g). Elution with hexane (10 mL) gave a small quantity of less polar compounds; further elution with hexane/ethyl acetate (9:1) provided the silylated ketone. Final purification was achieved by HPLC (10-mm×25-cm Zorbax-Sil column, 4 mL/min) using hexane/ethyl acetate (95:5) solvent system. Pure protected hydroxy ketone 42 (9.4 mg, 46%) was eluted at $R_v$ 39 mL as a colorless oil: $^1H$ NMR ($CDCl_3$) 0.576 (6H, q, J=7.9 Hz, 3×$SiCH_2$), 0.638 (3H, s, 18-$H_3$), 0.865 (3H, d, J=6.1 Hz, 21-$H_3$), 0.949 (9H, t, J=7.9 Hz, 3×$SiCH_2CH_3$), 2.45 (1H, dd, J=11.4, 7.5 Hz, 14α-H).

20(S)-1α,25-Dihydroxy-26,27-dimethylene-2-methylene-19-norvitamin $D_3$ (47). To a solution of phosphine oxide 43 (17.7 mg, 30.4 μmol) in anhydrous THF (300 μL) at 0° C. was slowly added n-BuLi (2.5 M in hexanes, 13 μL, 32.5 μmol) under argon with stirring. The solution turned deep orange. It was stirred for 10 min at 0° C., then cooled to −78° C. and a precooled (−78° C.) solution of protected hydroxy ketone 41 (17.8 mg, 42.3 μmol) in anhydrous THF (300+100 μL) was slowly added. The mixture was stirred under argon at −78° C. for 1.5 h and at 0° C. for 18 h. Water and ethyl acetate were added, and the organic phase was washed with brine, dried ($MgSO_4$) and evaporated. The residue was dissolved in hexane and applied on a silica Sep-Pak cartridge, and washed with hexane/ethyl acetate (99.7:0.3, 20 mL) to give slightly impure 19-norvitamin derivative 44 (ca. 11 mg). The Sep-Pak was then washed with hexane/ethyl acetate (96:4, 10 mL) to recover some unchanged C,D-ring ketone (contaminated with 14β-isomer), and with ethyl acetate (10 mL) to recover diphenylphosphine oxide 43 (ca. 8 mg) that was subsequently purified by HPLC (10-mm×25-cm Zorbax-Sil column, 4 mL/min) using hexane/2-propanol (9:1) solvent system; pure compound 43 (7.6 mg) was eluted at $R_v$ 36 mL. The protected vitamin 44 was further purified by HPLC (6.2-mm×25-cm Zorbax-Sil column, 4 mL/min) using hexane/ethyl acetate (99.9:0.1) solvent system. Pure compound 44 (10.1 mg, 74% yield considering the recovery of unreacted 43) was eluted at $R_v$ 27 mL as a colorless oil: UV (in hexane) $_{max}$ 244.0, 252.5, 262.5 nm; $^1H$ NMR ($CDCl_3$) δ 0.027, 0.048, 0.067, and 0.080 (each 3H, each s, 4×$SiCH_3$), 0.544 (3H, s, 18-$H_3$), 0.575 (6H, q, J=7.9 Hz, 3×$SiCH_2$), 0.854 (3H, d, J=6.1 Hz, 21-$H_3$), 0.866 and 0.896 (9H and 9H, each s, 2×Si-t-Bu), 0.947 (9H, t, J=7.9 Hz, 3×$SiCH_2CH_3$), 1.99 (2H, m), 2.18 (1H, dd, J=12.8, 8.6 Hz, 4β-H), 2.34 (1H, dd, J=13.2, 2.7 Hz, 10β-H), 2.46 (1H, dd, J=12.8, 4.4 Hz, 4α-H), 2.51 (1H, dd, J=13.2, 6.0 Hz, 10α-H), 2.82 (1H, br d, J=12 Hz, 9β-H), 4.42 (2H, m, 1β- and 3α-H), 4.92 and 4.97 (1H and 1H, each s, =$CH_2$), 5.84 and 6.22 (1H and 1H, each d, J=11.2 Hz, 7- and 6-H); MS m/z (relative intensity) 784 ($M^+$, 8), 755 ($M^+$-Et, 4), 727 ($M^+$-t-Bu, 6), 652 (100), 520 (31), 366 (49), 199 (23).

Protected vitamin 44 (7.0 mg) was dissolved in benzene (220 μL) and the resin (AG 50W-X4, 95 mg; prewashed with methanol) in methanol (1.2 mL) was added. The mixture was stirred at room temperature under argon for 21 h, diluted with ethyl acetate/ether (1:1, 4 mL) and decanted. The resin was washed with ether (10 mL) and the combined organic phases washed with brine and saturated $NaHCO_3$, dried ($MgSO_4$) and evaporated. The residue was separated by HPLC (6.2-mm×25-cm Zorbax-Sil column, 4 mL/min) using hexane/2-propanol (9:1) solvent system and the following analytically pure 2-methylene-19-norvitamins were isolated: 1α-hydroxy-25-dehydrovitamin 45 (0.68 mg, 17%) was collected at $R_v$ 13 mL, 1α-hydroxy-25-methoxyvitamin 46 (0.76 mg, 19%) was collected at $R_v$ 16 mL and 1α,25-dihydroxyvitamin 47 (2.0 mg, 51%) was collected at $R_v$ 21 mL.

45: UV (in EtOH) $\lambda_{max}$ 243.5, 251.5, 262.0 nm; $^1H$ NMR ($CDCl_3$) δ 0.542 (3H, s, 18-$H_3$), 0.847 (3H, d, J=6.5 Hz, 21-$H_3$), 1.93–2.07 (4H, m), 2.18–2.25 (2H, m), 2.26–2.36 (4H, m), 2.58 (1H, dd, J=13.3, 3.9 Hz, 4α-H), 2.82 (1H, br d, J=13 Hz, 9β-H), 2.85 (1H, dd, J=13.3, 4.5 Hz, 10β-H), 4.48 (2H, m, 1β- and 3α-H), 5.09 and 5.11 (1H and 1H, each s, =$CH_2$), 5.32 (1H, m, w/2=7 Hz, 24-H), 5.88 and 6.36 (1H and 1H, each d, J=11.1 Hz, 7- and 6-H); MS m/z (relative intensity) 424 ($M^+$, 100), 406 (7), 339 (16), 287 (16), 271 (24), 269 (17), 251 (12); exact mass calcd for $C_{29}H_{44}O_2$ 424.3341, found 424.3343.

46: UV (in EtOH) $\lambda_{max}$ 243.5, 252.0, 262.0 nm; $^1H$ NMR ($CDCl_3$) δ 0.553 (3H, s, 18-$H_3$), 0.858 (3H, d, J=6.5 Hz, 21-$H_3$), 1.95–2.05 (2H, m), 2.30 (1H, dd, J=13.3, 8.3 Hz, 10α-H), 2.33 (1H, dd, J=13.4, 6.0 Hz, 4β-H), 2.58 (1H, dd, J=13.4, 3.8 Hz, 4α-H), 2.82 (1H, br d, J=13 Hz, 9β-H), 2.85 (1H, dd, J=13.3, 4.4 Hz, 10β-H), 3.13 (3H, s, $OCH_3$), 4.48 (2H, m, 1β- and 3α-H), 5.09 and 5.11 (1H and 1H, each s, =$CH_2$), 5.89 and 6.36 (1H and 1H, each d, J=11.2 Hz, 7- and 6-H); MS m/z (relative intensity) 456 ($M^+$, 54), 424 (27), 406 (12), 339 (16), 287 (13), 271 (41), 99 (100); exact mass calcd for $C_{30}H_{48}O_3$ 456.3603, found 456.3603.

47: UV (in EtOH) $_{max}$ 243.5, 252.0, 262.0 nm; $^1H$ NMR ($CDCl_3$) δ 0.551 (3H, s, 18-$H_3$), 0.859 (3H, d, J=6.6 Hz, 21-$H_3$), 1.95–2.05 (2H, m), 2.30 (1H, dd, J=13.5, 8.4 Hz, 10α-H), 2.33 (1H, dd, J=13.3, 6.3 Hz, 4β-H), 2.58 (1H, dd, J=13.3, 4.0 Hz, 4α-H), 2.82 (1H, br d, J=12 Hz, 9β-H), 2.85 (1H, dd, J=13.5, 4.4 Hz, 10β-H), 4.48 (2H, m, 1β- and 3α-H), 5.09 and 5.11 (1H and 1H, each s, =$CH_2$), 5.89 and 6.36 (1H and 1H, each d, J=11.3 Hz, 7- and 6-H); MS m/z (relative intensity) 442 ($M^+$, 100), 424 (47), 406 (15), 339 (34), 287 (27), 271 (42), 269 (36), 251 (26); exact mass calcd for $C_{29}H_{46}O_3$ 442.3447, found 442.3442.

BIOLOGICAL ACTIVITY OF 20(S)-26,27-DIMETHYLENE-1α-HYDROXY-2-METHYLENE-24-DEHYDRO-19-NORVITAMIN $D_3$ (45); 20(S)-26,27-DIMETHYLENE-1α-HYDROXY-25-METHOXY-2-METHYLENE-19-NORVITAMIN $D_3$ (46); AND 20(S)-1α,25-DIHYDROXY-26,27-DIMETHYLENE-2-METHYLENE-19-NORVITAMIN $D_3$ (47)

Competitive binding of the analogs to the porcine intestinal receptor was carried out by the method described by Dame et al (Biochemistry 25, 4523–4534, 1986).

The differentiation of HL-60 promyelocytic into monocytes was determined as described by Ostrem et al (J. Biol. Chem. 262, 14164–14171, 1987).

TABLE 5

VDR Binding Properties[a] and HL-60 Differentiating Activities[b] of Side Chain Analogs of 20(S)-26,27-dimethylene-1α-hydroxy-2-methylene-19-norvitamin $D_3$

| Compound | Compd. no. | VDR Binding $ED_{50}$ (M) | Binding ratio | HL-60 Differentiation $ED_{50}$ (M) | Activity ratio |
|---|---|---|---|---|---|
| 1α,25-$(OH)_2D_3$ | | $8.7 \times 10^{-10}$ | 1 | $4.0 \times 10^{-9}$ | 1 |
| 26,27-dimethylene-2-methylene-24-dehydro-19-nor-20(S)-1α-OH-$D_3$ | 45 | $2.9 \times 10^{-8}$ | 33 | $4.1 \times 10^{-9}$ | 1.0 |
| 26,27-dimethylene-2-methylene-25-methoxy-19-nor-20(S)-1α-OH-$D_3$ | 46 | $1.5 \times 10^{-8}$ | 17 | $4.3 \times 10^{-9}$ | 1.1 |
| 26,27-dimethylene-2-methylene-19-nor-20(S)-1α,25-$(OH)_2D_3$ | 47 | $2.7 \times 10^{-9}$ | 3.1 | $3.6 \times 10^{-11}$ | 0.01 |

[a]Competitive binding of 1α,25-$(OH)_2D_3$ and the synthesized vitamin D analogs to the porcine intestinal vitamin D receptor. The experiments were carried out in triplicate on two different occasions. The $ED_{50}$ values are derived from dose-response curves and represent the analog concentration required for 50% displacement of the radiolabeled 1α,25-$(OH)_2D_3$ from the receptor protein. Binding ratio is the ratio of the analog average $ED_{50}$ to the $ED_{50}$ for 1α,25-$(OH)_2D_3$.
[b]Induction of differentiation of HL-60 promyelocytes to monocytes by 1α,25-$(OH)_2D_3$ and the synthesized vitamin D analogs. Differentiation state was determined by measuring the percentage of cells reducing nitro blue tetrazolium (NBT). The experiment was repeated three times. The values $ED_{50}$ are derived from dose-response curves and represent the analog concentration capable of inducing 50% maturation. Differentiation activity radio is the ratio of the analog average $ED_{50}$ to the $ED_{50}$ for 1α,25-$(OH)_2D_3$.

TABLE 6

Support of Intestinal Calcium Transport and Bone Calcium Mobilization by Side Chain Analogs of 20(S)-26,27-dimethylene-1α-hydroxy-2-methylene-19-norvitamin $D_3$ in Vitamin D-Deficient Rats on a Low-Calcium Diet[a]

| Compound | Compd. no. | Amount (pmol) | Ca Transport S/M (mean ± SEM) | Serum Ca (mean ± SEM) |
|---|---|---|---|---|
| none (control) | | 0 | $2.7 \pm 0.3^b$ | $4.7 \pm 0.2^b$ |
| 1α,25-$(OH)_2D_3$ | | 260 | $7.2 \pm 0.6^c$ | $5.6 \pm 0.2^c$ |
| 26,27-dimethylene-2-methylene-19-nor-20(S)-1α,25-$(OH)_2D_3$ | 47 | 15 | $5.6 \pm 0.6^{d1}$ | $5.4 \pm 0.2^{d1}$ |
| | | 32 | $5.3 \pm 0.5^{d2}$ | $6.4 \pm 0.2^{d2}$ |
| none (control) | | 0 | $3.6 \pm 0.4^b$ | $5.0 \pm 0.1^b$ |
| 1α,25-$(OH)_2D_3$ | | 260 | $5.0 \pm 0.4^c$ | $6.3 \pm 0.2^c$ |
| 26,27-dimethylene-2-methylene-24-dehydro-19-nor-20(S)-1α-OH-$D_3$ | 45 | 65 | $5.5 \pm 0.8^{d1}$ | $5.7 \pm 0.1^{d1}$ |
| | | 260 | $4.3 \pm 0.5^{d2}$ | $10.8 \pm 0.3^{d2}$ |
| 26,27-dimethylene-2-methylene-25-methoxy-19-nor-20(S)-1α-OH-$D_3$ | 46 | 65 | $5.5 \pm 0.8^{e1}$ | $5.7 \pm 0.1^{e1}$ |
| | | 260 | $4.3 \pm 0.5^{e2}$ | $10.8 \pm 0.3^{e2}$ |

[a]Weanling male rats were maintained on a 0.47% Ca diet for 1 week and then switched to a low-calcium diet containing 0.02% Ca for an additional 3 weeks. During the last week, they were dosed daily with the appropriate vitamin D compound for 7 consecutive days. All doses were administered intraperitoneally in 0.1 ml propylene glycol/ethanol (95:5). Controls received the vehicle. Determinations were made 24 h after the last dose. There were at least 6 rats per group. Statistical analysis was done by Student's t-test. Statistical data: serosal/mucosal (S/M), panel 1, b from c, $p < 0.001$, b from $d^1$ and $d^2$, $p = 0.001$; panel 2, b from c and $e^1$, $p < 0.05$, b from $d^1$, $d^2$, and $e^2$, NS; serum calcium, panel 1, b from c, $p < 0.05$, b from $d^1$, NS, b from $d^2$, $p = 0.005$; panel 2, b from c, $p < 0.01$, b from $d^1$, NS, b from $d^2$ and $e^1$, $p = 0.05$, b from $e^2$, $p < 0.001$.

For treatment purposes, the novel compounds of this invention defined by formula I may be formulated for pharmaceutical applications as a solution in innocuous solvents, or as an emulsion, suspension or dispersion in suitable solvents or carriers, or as pills, tablets or capsules, together with solid carriers, according to conventional methods known in the art. Any such formulations may also contain other pharmaceutically-acceptable and non-toxic excipients such as stabilizers, anti-oxidants, binders, coloring agents or emulsifying or taste-modifying agents.

The compounds may be administered orally, topically, parenterally or transdermally. The compounds are advantageously administered by injection or by intravenous infusion or suitable sterile solutions, or in the form of liquid or solid doses via the alimentary canal, or in the form of creams, ointments, patches, or similar vehicles suitable for transdermal applications. Doses of from 0.1 μg to 50 μg per day of the compounds are appropriate for treatment purposes, such doses being adjusted according to the disease to be treated, its severity and the response of the subject as is well understood in the art. Since the new compounds exhibit specificity of action, each may be suitably administered alone, or together with graded doses of another active vitamin D compound—e.g. 1α-hydroxyvitamin $D_2$ or $D_3$, or 1α,25-dihydroxyvitamin $D_3$—in situations where different degrees of bone mineral mobilization and calcium transport stimulation is found to be advantageous.

Compositions for use in the above-mentioned treatment of psoriasis and other malignancies comprise an effective amount of one or more 2-alkylidene-19-nor-vitamin D compound as defined by the above formula I as the active ingredient, and a suitable carrier. An effective amount of such compounds for use in accordance with this invention is from about 0.01 μg to about 100 μg per gm of composition, and may be administered topically, transdermally, orally or parenterally in dosages of from about 0.1 μg/day to about 100μg/day.

The compounds may be formulated as creams, lotions, ointments, topical patches, pills, capsules or tablets, or in liquid form as solutions, emulsions, dispersions, or suspensions in pharmaceutically innocuous and acceptable solvent or oils, and such preparations may contain in addition other pharmaceutically innocuous or beneficial components, such as stabilizers, antioxidants, emulsifiers, coloring agents, binders or taste-modifying agents.

The compounds are advantageously administered in amounts sufficient to effect the differentiation of promyelocytes to normal macrophages. Dosages as described above are suitable, it being understood that the amounts given are to be adjusted in accordance with the severity of the disease, and the condition and response of the subject as is well understood in the art.

The formulations of the present invention comprise an active ingredient in association with a pharmaceutically acceptable carrier therefore and optionally other therapeutic ingredients. The carrier must be "acceptable" in the sense of being compatible with the other ingredients of the formulations and not deleterious to the recipient thereof.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion.

Formulations for rectal administration may be in the form of a suppository incorporating the active ingredient and carrier such as cocoa butter, or in the form of an enema.

Formulations suitable for parenteral administration conveniently comprise a sterile oily or aqueous preparation of the active ingredient which is preferably isotonic with the blood of the recipient.

Formulations suitable for topical administration include liquid or semi-liquid preparations such as liniments, lotions, applicants, oil-in-water or water-in-oil emulsions such as creams, ointments or pastes; or solutions or suspensions such as drops; or as sprays.

For asthma treatment, inhalation of powder, self-propelling or spray formulations, dispensed with a spray can, a nebulizer or an atomizer can be used. The formulations, when dispensed, preferably have a particle size in the range of 10 to 100μ.

The formulations may conveniently be presented in dosage unit form and may be prepared by any of the methods well known in the art of pharmacy. By the term "dosage unit" is meant a unitary, i.e. a single dose which is capable of being administered to a patient as a physically and chemically stable unit dose comprising either the active ingredient as such or a mixture of it with solid or liquid pharmaceutical diluents or carriers.

In its broadest application, the present invention relates to any 19-nor-2-alkylidene analogs of vitamin D which have the vitamin D nucleus. By vitamin D nucleus, it is meant a central part consisting of a substituted chain of five carbon atoms which correspond to positions 8, 14, 13, 17 and 20 of vitamin D, and at the ends of which are connected at position 20 a structural moiety representing any of the typical side chains known for vitamin D type compounds (such as R as previously defined herein), and at position 8 the 5,7-diene moiety connected to the A-ring of an active 1α-hydroxy vitamin D analog (as illustrated by formula I herein). Thus, various known modifications to the six-membered C-ring and the five-membered D-ring typically present in vitamin D, such as the lack of one or the other or both, are also embraced by the present invention.

Accordingly, compounds of the following formulae Ia, are along with those of formula I, also encompassed by the present invention:

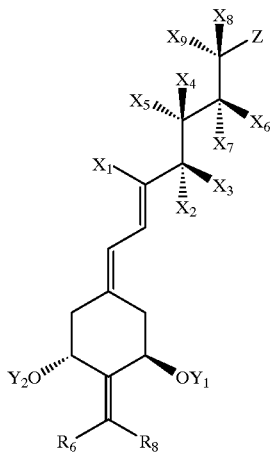

Ia

In the above formula Ia, the definitions of $Y_1$, $Y_2$, $R_6$, $R_8$ and Z are as previously set forth herein. With respect to $X_1$, $X_2$, $X_3$, $X_4$, $X_5$, $X_6$, $X_7$, $X_8$ and $X_9$, these substituents may be the same or different and are selected from hydrogen or lower alkyl, i.e. a $C_{1-5}$ alkyl such as methyl, ethyl or n-propyl. In addition, paired substituents $X_1$ and $X_4$ or $X_5$, $X_2$ or $X_3$ and $X_6$ or $X_7$, $X_4$ or $X_5$ and $X_8$ or $X_9$, when taken together with the three adjacent carbon atoms of the central part of the compound, which correspond to positions 8, 14, 13 or 14, 13, 17 or 13, 17, 20 respectively, can be the same or different and form a saturated or unsaturated, substituted or unsubstituted, carbocyclic 3, 4, 5, 6 or 7 membered ring.

Preferred compounds of the present invention may be represented by one of the following formulae:

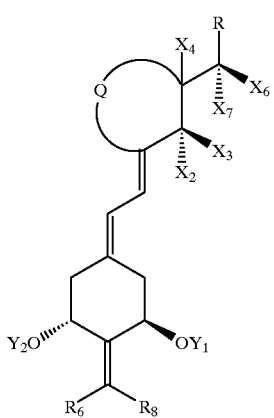

Ib

Ic
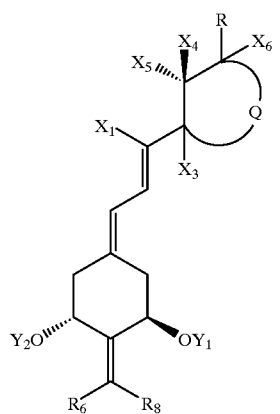
Id
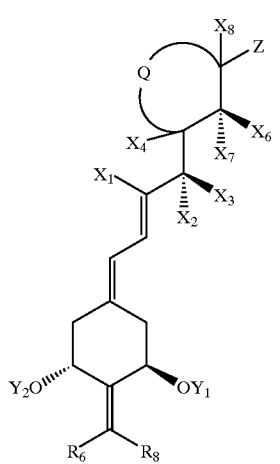
Ie
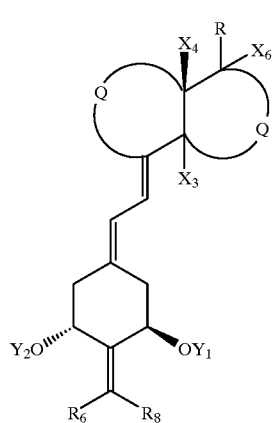
If
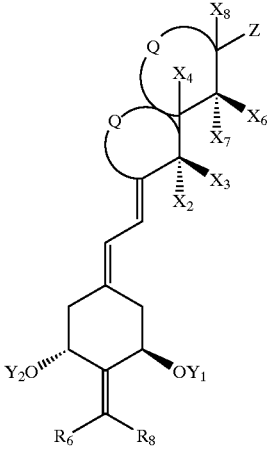
Ig
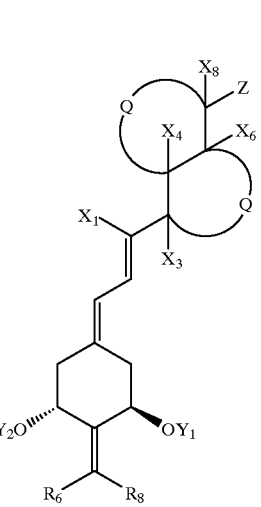
Ih
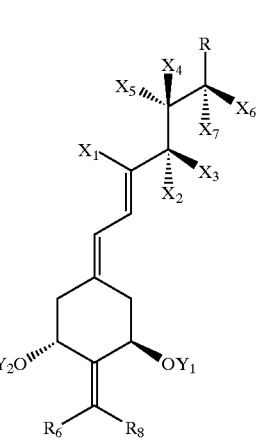

In the above formulae Ib, Ic, Id, Ie, If, Ig and Ih, the definitions of $Y_1$, $Y_2$, $R_6$, $R_8$, R, Z, $X_1$, $X_2$, $X_3$, $X_4$, $X_5$, $X_6$, $X_7$ and $X_8$ are as previously set forth herein. The substituent Q represents a saturated or unsaturated, substituted or unsubstituted, hydrocarbon chain comprised of 0, 1, 2, 3 or 4 carbon atoms, but is preferably the group —$(CH_2)_k$— where k is an integer equal to 2 or 3.

Methods for making compounds of formulae Ia–Ih are known. Specifically, –reference is made to International Application Number PCT/EP94/02294 filed Jul. 7, 1994 and published Jan. 19, 1995 under Ineratonal Publication Number WO95/01960.

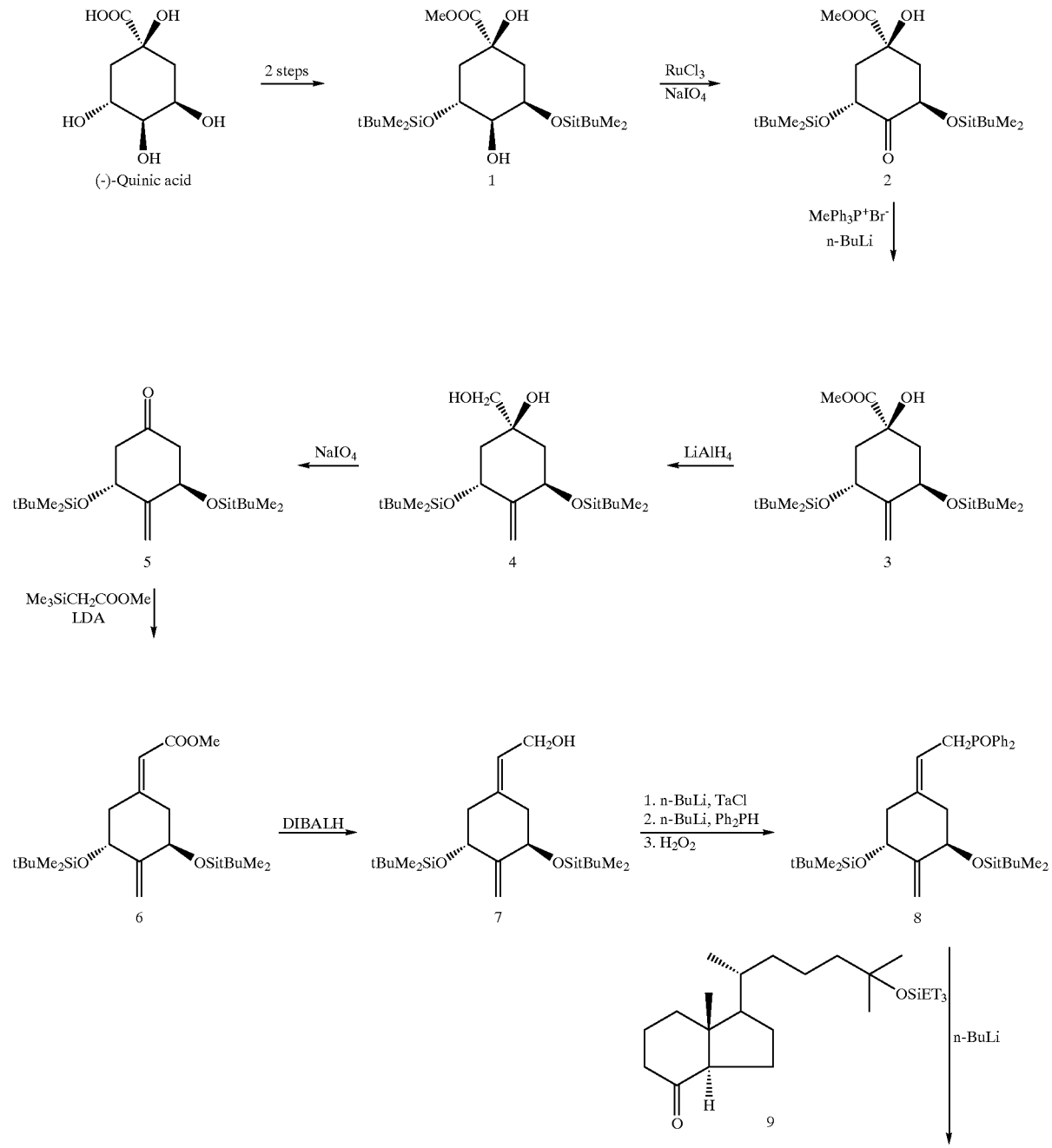

SCHEME I 31    32
-continued
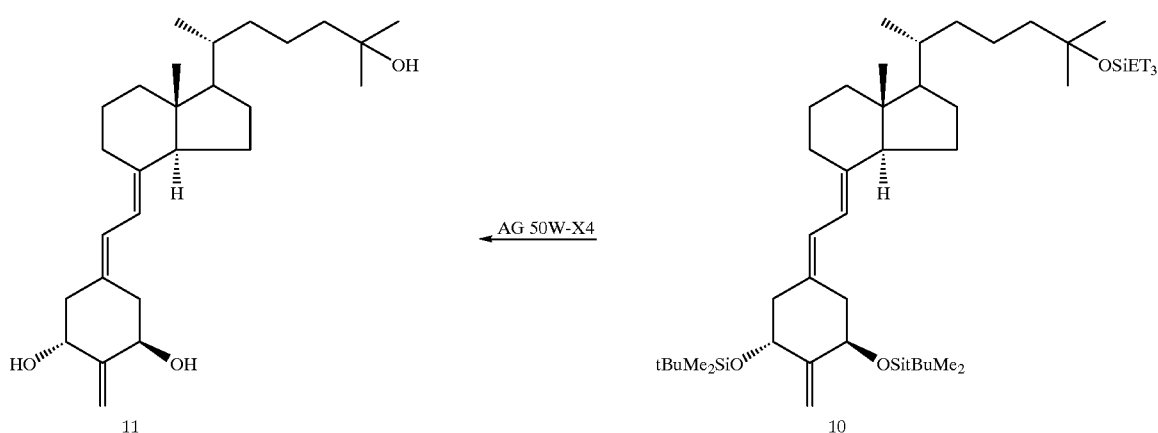
SCHEME II
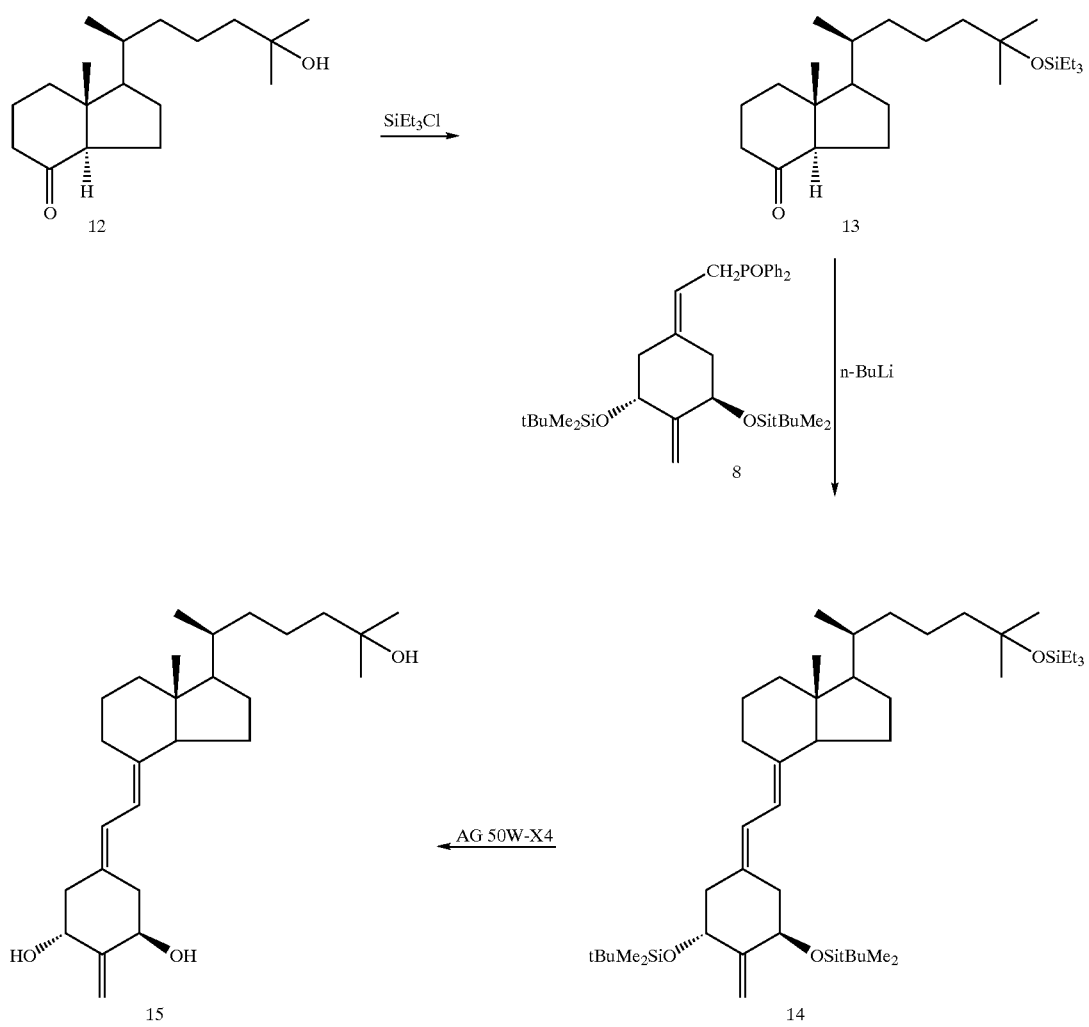

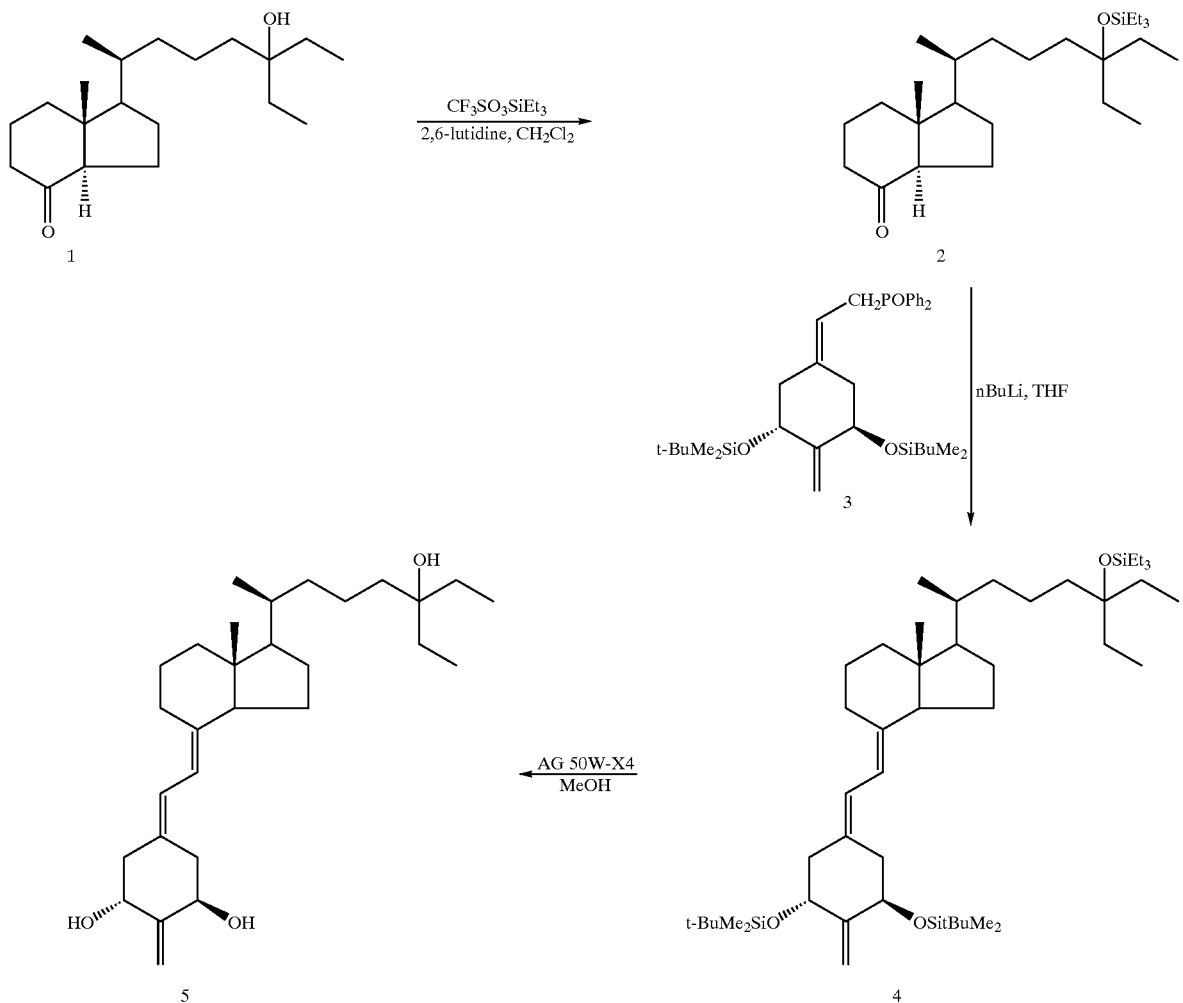
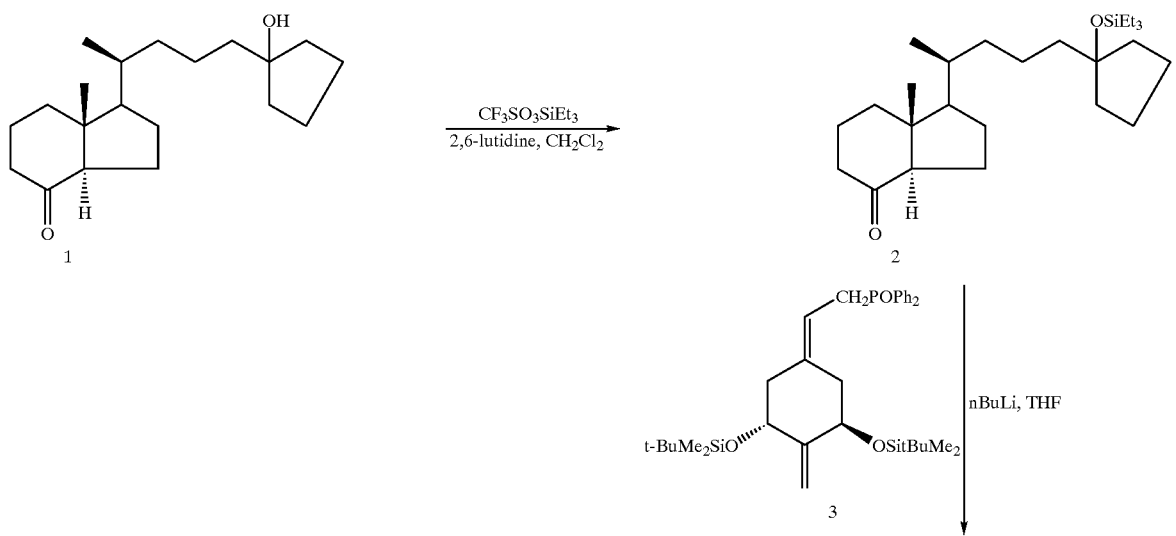

-continued

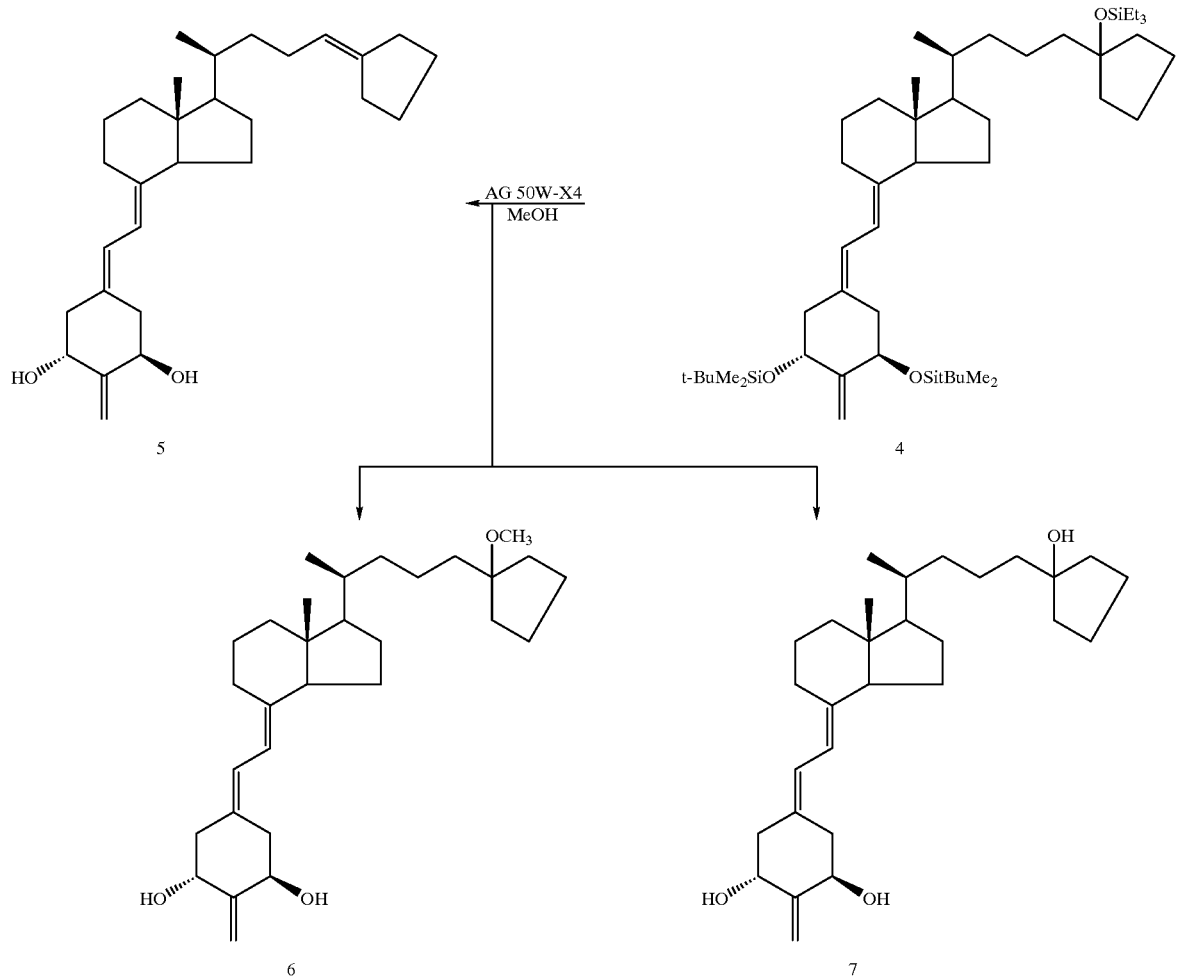

We claim:
1. 20(S)-1α,25-dihydroxy-2-methylene-26,27-dihomo-19-norvitamin $D_3$.
2. 20(S)-26,27-dimethylene-25-methoxy-2-methylene-19-norvitamin $D_3$.
3. 20(S)-1α,25-dihydroxy-26,27-dimethylene-2-methylene-19-norvitamin $D_3$.
4. 20(S)-26,27-dimethylene-1α-hydroxy-2-methylene-24-dehydro-19-norvitamin $D_3$.
5. A pharmaceutical composition containing at least one compound selected from the group consisting of
   20(S)-1α,25-dihydroxy-2-methylene-26,27-dihomo-19-norvitamin $D_3$,
   20(S)-26,27-dimethylene-25-methoxy-2-methylene-19-norvitamin $D_3$,
   20(S)-1α,25-dihydroxy-26,27-dimethylene-2-methylene-19-norvitamin $D_3$, and
   20(S)-26,27-dimethylene-1α-hydroxy-2-methylene-24-dehydro-19-norvitamin $D_3$, together with a pharmaceutically acceptable excipient.

6. The pharmaceutical composition of claim 5 containing 20(S)-1α,25-dihydroxy-2-methylene-26,27-dihomo-19-norvitamin $D_3$ in an amount from about 0.1 μg to about 50 μg.
7. The pharmaceutical composition of claim 5 containing 20(S)-26,27-dimethylene-25-methoxy-2-methylene-19-norvitamin $D_3$ in an amount from about 0.1 μg to about 50 μg.
8. The pharmaceutical composition of claim 5 containing 20(S)-1α,25-dihydroxy-26,27-dimethylene-2-methylene-19-norvitamin $D_3$ in an amount of from about 0.1 μg to about 50 μg.
9. The pharmaceutical composition of claim 5 containing 20(S)-26,27-dimethylene-1α-hydroxy-2-methylene-24-dehydro-19-norvitamin $D_3$ in an amount from about 0.1 μg to about 50 μg.

* * * * *

UNITED STATES PATENT AND TRADEMARK OFFICE
CERTIFICATE OF CORRECTION

PATENT NO. : 6,392,071 B1 Page 1 of 1
APPLICATION NO. : 09/540686
DATED : May 21, 2002
INVENTOR(S) : Hector F. DeLuca et al.

It is certified that error appears in the above-identified patent and that said Letters Patent is hereby corrected as shown below:

IN THE CLAIMS:

Claim 2, col. 35, line 44   After "20(S)-26,27-dimethylene-"

Insert --1α-hydroxy--

Signed and Sealed this

Thirtieth Day of January, 2007

JON W. DUDAS
*Director of the United States Patent and Trademark Office*